US012746095B2

(12) United States Patent
Arai et al.

(10) Patent No.: US 12,746,095 B2
(45) Date of Patent: Sep. 29, 2026

(54) MEDICAL ARM DEVICE

(71) Applicant: Sony Group Corporation, Tokyo (JP)

(72) Inventors: Jun Arai, Tokyo (JP); Kei Tomatsu, Tokyo (JP); Kazuo Hongo, Tokyo (JP)

(73) Assignee: Sony Group Corporation, Tokyo (JP)

( * ) Notice: Subject to any disclaimer, the term of this patent is extended or adjusted under 35 U.S.C. 154(b) by 408 days.

(21) Appl. No.: 18/000,823

(22) PCT Filed: May 18, 2021

(86) PCT No.: PCT/JP2021/018803
§ 371 (c)(1),
(2) Date: Dec. 6, 2022

(87) PCT Pub. No.: WO2022/009528
PCT Pub. Date: Jan. 13, 2022

(65) Prior Publication Data

US 2023/0218365 A1 Jul. 13, 2023

(30) Foreign Application Priority Data

Jul. 9, 2020 (JP) ................................ 2020-118524

(51) Int. Cl.
*A61B 90/50* (2016.01)
*A61B 90/00* (2016.01)

(52) U.S. Cl.
CPC ............ *A61B 90/50* (2016.02); *A61B 90/361* (2016.02)

(58) Field of Classification Search
None
See application file for complete search history.

(56) References Cited

U.S. PATENT DOCUMENTS 5,372,147 A * 12/1994 Lathrop, Jr. ........... A61B 34/30 600/230
6,949,106 B2 * 9/2005 Brock ................ A61B 17/0469 606/130

(Continued)

FOREIGN PATENT DOCUMENTS

CN 207613874 U 7/2018
JP H07289563 A 11/1995

(Continued)

OTHER PUBLICATIONS

International Search Report and Written Opinion mailed on Jul. 27, 2021, received for PCT Application No. PCT/JP2021/018803, filed on May 18, 2021, 10 pages including English Translation.

*Primary Examiner* — Shaun L David
(74) *Attorney, Agent, or Firm* — XSENSUS LLP

(57) ABSTRACT

Provided is a medical arm device that avoids interference with a surgeon.
A medical arm device includes a first arm part including a tip part that supports a medical instrument such as an endoscope, and a second arm part that supports the first arm part, and includes at least two horizontal rotation axes and an inter-axis distance changing unit that changes a distance between the two horizontal rotation axes. The tip part includes a structure in which joint members corresponding to rotation axes of three degrees of freedom that determine an attitude of the medical instrument are directly connected, and a rotation axis around a longitudinal axis of the medical instrument, a yaw axis in a case where the rotation axis around the longitudinal axis is a roll axis, and a pitch axis are disposed in order from a most tip part.

20 Claims, 24 Drawing Sheets

(56) References Cited

U.S. PATENT DOCUMENTS

| | | | | |
|---|---|---|---|---|
| 2011/0071473 | A1* | 3/2011 | Rogers | A61M 39/02<br>604/164.01 |
| 2013/0325033 | A1 | 12/2013 | Schena | |
| 2015/0250547 | A1* | 9/2015 | Fukushima | A61B 90/361<br>606/130 |
| 2016/0100896 | A1* | 4/2016 | Yu | A61B 34/30<br>606/130 |
| 2017/0172670 | A1* | 6/2017 | Swarup | A61B 34/30 |
| 2018/0200006 | A1 | 7/2018 | Kamikawa | |
| 2019/0328475 | A1 | 10/2019 | Arai | |
| 2019/0328479 | A1* | 10/2019 | Wada | A61B 90/25 |
| 2019/0365489 | A1* | 12/2019 | Kasai | A61B 1/055 |
| 2020/0046441 | A1 | 2/2020 | Liu et al. | |

FOREIGN PATENT DOCUMENTS

| | | | |
|---|---|---|---|
| JP | 10-277055 | A | 10/1998 |
| JP | 2003-19217 | A | 1/2003 |
| JP | 2015-525095 | A | 9/2015 |
| JP | 2018-75121 | A | 5/2018 |

* cited by examiner

MEDICAL ARM DEVICE

CROSS-REFERENCE TO RELATED APPLICATIONS

The present application is based on PCT filing PCT/JP2021/018803, filed May 18, 2021, which claims priority to Japanese Application No. 2020-118524, filed Jul. 9, 2020, the entire contents of each are incorporated herein by reference.

TECHNICAL FIELD

The technology disclosed in the present specification (hereinafter, "the present disclosure") relates to a medical arm device used to support a medical instrument, for example, in a medical field.

BACKGROUND ART

In laparoscopic surgery, trocars are attached to several small holes bored in the abdomen of a patient, for example, and medical instruments such as an endoscope and forceps are inserted into an abdominal cavity via the trocars, and a surgeon performs surgery while watching a video imaged by the endoscope. Since the laparoscopic surgery does not require laparotomy, a burden on the patient is small and postoperative recovery is quick, and the number of days until discharge is greatly reduced.

In laparoscopic surgery, adjustment of a field of view of the endoscope or the like affects the progress of surgery, but a control technique is not constant for each operator (scopist). For this reason, by introducing a medical arm device that supports the endoscope, cost reduction such as labor cost of a scopist, high accuracy of a control technique of the endoscope, and improvement of safety are achieved.

For example, a medical support arm device including a plurality of active joint units that connects a plurality of links and is driven by an actuator to change an attitude of an arm part including the plurality of links, a torque sensor that detects torque acting on the active joint units, and at least one passive form change mechanism that can change a form of the arm part has been proposed (See Patent Document 1.).

CITATION LIST

Patent Document

Patent Document 1: Japanese Patent Application Laid-Open No. 2018-75121

SUMMARY OF THE INVENTION

Problems to be Solved by the Invention

An object of the present disclosure is to provide a medical arm device that is used for, for example, laparoscopic surgery and supports a medical instrument such as an endoscope.

Solutions to Problems

The present disclosure is directed to a medical arm device including:

- a first arm part including a tip part that supports a medical instrument; and
- a second arm part that supports the first arm part, and includes at least two horizontal rotation axes and an inter-axis distance changing unit that changes a distance between the two horizontal rotation axes. The medical instrument is, for example, a medical observation device including an imaging unit such as an endoscope.

The second arm part includes a first link, a first joint part having a degree of freedom around a horizontal rotation axis at a tip of the first link, a second link horizontally attached to the tip of the first link via the first joint part, and a second joint part having a degree of freedom around a horizontal rotation axis at a tip of the second link. Furthermore, the second link includes the inter-axis distance changing unit, and the first arm part is supported via the second joint part.

The tip part includes a structure in which joint members corresponding to rotation axes of three degrees of freedom that determine an attitude of the endoscope are directly connected. The tip part includes a structure in which a rotation axis around a longitudinal axis of the medical instrument, a yaw axis in a case where the rotation axis around the longitudinal axis is a roll axis, and a pitch axis are disposed in order from a most tip part.

Effects of the Invention

According to the present disclosure, it is possible to provide a medical arm device that supports a medical instrument such as an endoscope and avoids interference with a surgeon.

Note that the effects described in the present specification are merely examples, and the effects brought by the present disclosure are not limited thereto. Furthermore, the present disclosure may further provide additional effects in addition to the effects described above.

Still other objects, features, and advantages of the present disclosure will become apparent from a more detailed description based on embodiments as described later and the accompanying drawings.

MODE FOR CARRYING OUT THE INVENTION

Figure 1:
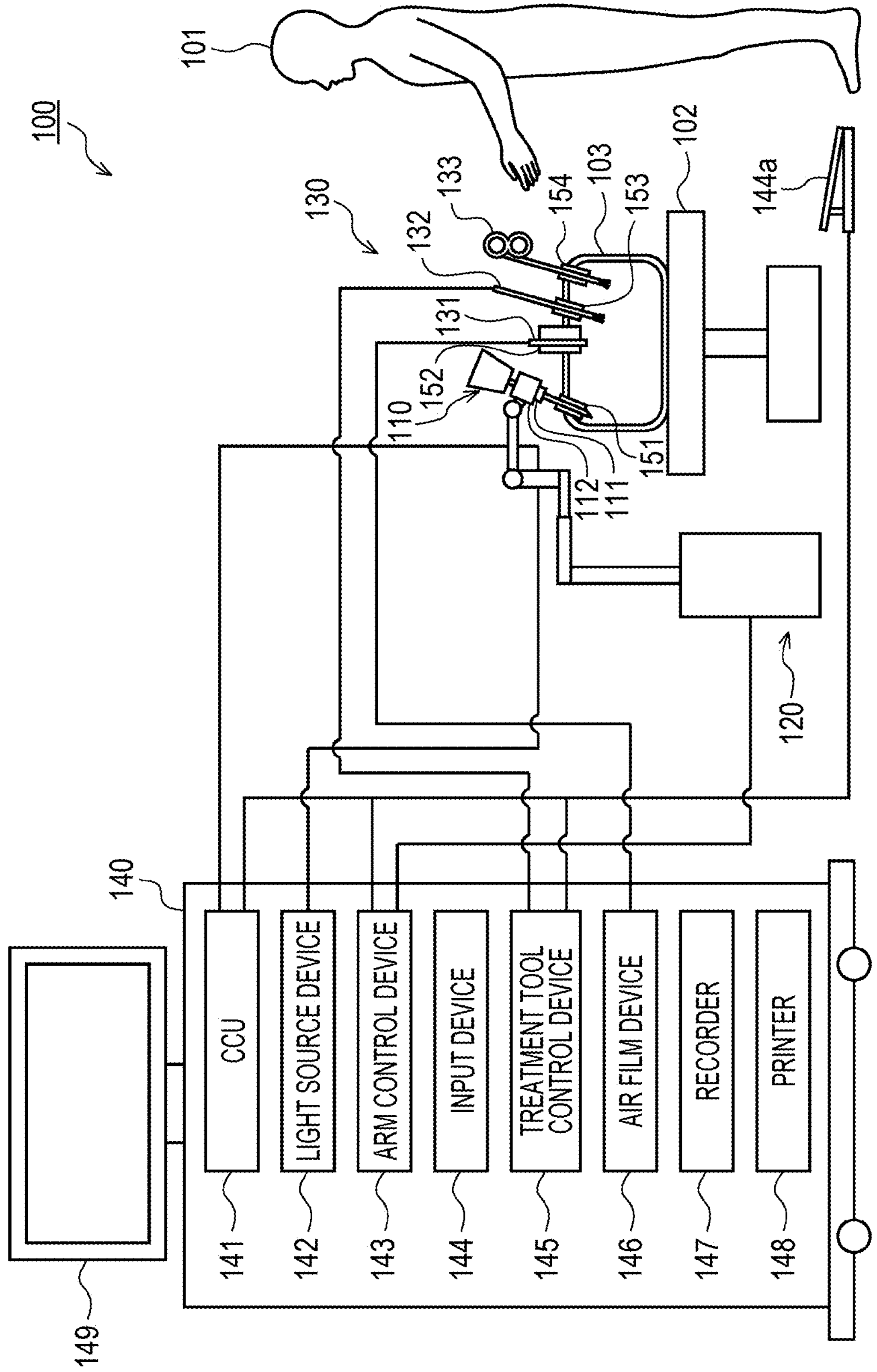
FIG. 1 is a diagram illustrating a configuration example of an endoscopic surgery system 100.

Hereinafter, the technology according to the present disclosure will be described in the following order with reference to the drawings.

A. Overview
B. Configuration of endoscopic surgery system
C. Camera head and CCU
D. Regarding endoscope
E. Medical arm device and arm control device
F. Configuration of medical arm device
G. Modification examples
H. Effects

A. Overview

The present disclosure realizes a medical arm device that satisfies the following three requirements, suppresses an increase in size of the device, and realizes a higher degree of freedom of an arm and a wider movable range.

(1) Capable of controlling an attitude of an endoscope with six degrees of freedom or more
(2) Ensure a sufficient operating range of the endoscope during surgery
(3) Correspond to various procedures The present disclosure realizes a medical arm device including a degree-of-freedom structure capable of avoiding interference with a surgeon in order to realize smooth cooperative work with the surgeon during surgery while satisfying the three requirements described above.

In general, in surgery using a medical arm device that supports a medical instrument such as an endoscope, since the hand of the surgeon is accessed from various directions such as obliquely front, side, or top of the surgeon, interference between the hand or arm of the surgeon and the arm is likely to occur.

A medical arm device according to the present disclosure includes a first arm part including a tip part that supports an endoscope, and a second arm part that supports the tip part, and the second arm part includes at least two horizontal rotation axes, and an inter-axis distance changing unit that changes a distance between the two horizontal rotation axes. Therefore, by adjusting the distance between the two horizontal rotation axes of the second arm part according to a direction of accessing the hand of the surgeon, it is possible to avoid interference between the surgeon's hand or arm and the arm tip part. In laparoscopic surgery, a scopist stands beside a surgeon to manipulate an endoscope. On the other hand, in the medical arm device according to the present disclosure, since the second arm part includes the inter-axis distance changing unit, it is possible to access a free space at the hand of the surgeon from an opposite side of the surgeon across a patient (or a surgical bed). In this manner, it is possible to avoid interference between the surgeon's hand or arm and the arm tip part by access from the surgeon's face.

Furthermore, the medical arm device according to the present disclosure has a structure in which orthogonal rotation axes with three degrees of freedom in which the tip part determines an attitude of the endoscope are intensively disposed. Here, the orthogonal rotation axes of three degrees of freedom have a structure in which an optical axis rotation axis of the endoscope, a pan axis for changing an observation direction of the endoscope, and a tilt axis are disposed in order from the most tip part. Alternatively, it can also be said that the orthogonal rotation axes of three degrees of freedom have a structure in which a rotation axis around a longitudinal axis of the endoscope, a yaw axis in a case where the rotation axis around the longitudinal axis is a roll axis, and a pitch axis are disposed in this order. Furthermore, the structure in which the rotation axes are intensively disposed is a structure in which joint members corresponding to the rotation axes of three degrees of freedom are directly connected, or a structure in which a distance between a joint corresponding to the rotation axis around the longitudinal axis and a joint corresponding to the pitch axis has a distance that does not cause interference when the rotation axis rotates around the pitch axis. As a result, it is possible to secure a sufficient operation range of the endoscope during surgery and to cope with various procedures.

B. Configuration of Endoscopic Surgery System

FIG. 1 schematically illustrates a configuration example of an endoscopic surgery system 100 to which a medical arm device according to the present disclosure can be applied. FIG. 1 illustrates a state where a surgeon (doctor) 101 is performing surgery on a patient 103 on a surgical bed 102 using the endoscopic surgery system 100. The endoscopic surgery system 100 includes an endoscope 110, a medical arm device 120 that supports the endoscope 110, a medical instrument group 130 other than the endoscope 110, and a cart 140 on which various devices for laparoscopic surgery are mounted.

The medical arm device 120 is basically an articulated arm (hereinafter, also simply referred to as an "arm") having a multilink structure in which a plurality of links is connected by joint axes. Although the medical arm device 120 supports the endoscope 110 at a tip part, as described in section A described above, the medical arm device has a degree-of-freedom structure capable of controlling an attitude of the endoscope 110 at six degrees of freedom or more, securing a sufficient operation range of the endoscope during surgery, coping with various manual works, and avoiding interference with the surgeon 101, but details will be described later.

Examples of the device mounted on the cart 140 include a camera control unit (CCU) 141, a light source device 142, an arm control device 143, an input device 144, a treatment tool control device 145, an air film device 146, a recorder 147, a printer 148, and a display device 149. However, a type of device mounted on the cart 140 can be appropriately changed according to a type of medical instrument used for the laparoscopic surgery.

In the laparoscopic surgery, instead of cutting and opening an abdominal wall of the patient 103, a lens barrel of the endoscope 110 and other medical instruments 131, 132, . . . are inserted into a body cavity of the patient 103 via a plurality of trocars 151, 152, . . . punctured into the abdominal wall. The medical instruments 131, 132, . . . are, for example, forceps, pneumoperitoneum tubes, energy treatment tools, tweezers, retractors, and the like, but are illustrated in a simplified manner in FIG. 1.

An image of a surgical site in the body cavity of the patient 103 imaged by the endoscope 110 is displayed on the display device 149. The surgeon 101 performs treatment such as resection of an affected part using the medical instruments 131, 132, . . . while viewing the image of the surgical site displayed on the display device 149 in real time. Furthermore, some (for example, forceps, a pneumoperitoneum tube, and an energy treatment tool) of the medical instruments 131, 132, . . . may be operated by an assistant (not illustrated) instead of the surgeon.

The endoscope 110 includes a lens barrel 111 inserted into the body cavity of the patient 103 at a tip, and a camera head 112 connected to a proximal end of the lens barrel 111. The lens barrel 111 is assumed to be a rigid mirror including a rigid lens barrel, but may be a flexible mirror including a flexible lens barrel. An optical system and an imaging element (both not illustrated) are disposed in the camera head 112. Reflected light (observation light) from an observation target such as a surgical site is imaged on the imaging element by the optical system. The imaging element photoelectrically converts the observation light, generates an image signal corresponding to an observation image, and transmits the image signal to the CCU 141. Note that the camera head 112 has a function of driving the optical system to adjust magnification and a focal length. Furthermore, a plurality of imaging elements may be disposed in the camera head 112 for stereoscopic viewing (3D display). In this case, a plurality of relay optical systems for guiding the observation light to the plurality of imaging elements is disposed inside the lens barrel 111.

The CCU 141 includes a processor such as a central processing unit (CPU) or a graphic processing unit (GPU), a local memory thereof, and the like, and comprehensively controls operations of the endoscope 110 and the display device 149. Specifically, the CCU 141 performs development processing such as demosaic on the image signal received from the camera head 112 and various image processing for displaying an image, and outputs the image signal to the display device 141. Furthermore, the CCU 141 transmits a control signal related to adjustment of the magnification and the focal length and an imaging condition to the camera head 112.

The display device 149 displays a captured image subjected to the image processing by the CCU 141 under the control of the CCU 141. It is preferable to use the display device 149 having an appropriate resolution or screen size according to the application. For example, in a case where the endoscope 110 supports high-resolution imaging such as 4K (the number of horizontal pixels 3840×the number of vertical pixels 2160) or 8K (the number of horizontal pixels 7680-×the number of vertical pixels 4320), or supports 3D display, it is preferable to use a display device capable of high-resolution or 3D display as the display device 149. By using a display device having a screen size of 55 inches or more as the display device 149 compatible with the high resolution of 4K or 8K, it is possible to give a further immersive feeling to an observer such as the surgeon 101.

The light source device 142 includes, for example, a light source such as a xenon lamp, a light emitting diode (LED), or a laser diode, and supplies illumination light to the endoscope 110 when imaging a surgical site.

The arm control device 143 controls driving of the medical arm device 120 according to a predetermined control method such as position control or force control. The medical arm device 120 has a multi-link structure in which a plurality of links is connected by joint axes, and at least a part of the joint axes is an active axis driven by an actuator. The arm control device 143 supplies a drive signal to each joint driving actuator. The arm control device 143 includes, for example, a processor such as a CPU and a local memory thereof, and controls driving of the medical arm device 120 by the processor executing a predetermined program loaded in the local memory.

The input device 144 is an input interface for the endoscopic surgery system 100. A user (for example, a surgeon or an assistant) can input various types of information and instructions to the endoscopic surgery system 100 via the input device 144. For example, the user inputs various types of information regarding surgery, such as physical information of the user and information regarding surgery, via the input device 144. Furthermore, the user inputs an instruction to drive the medical arm device 120, setting of imaging conditions (type of irradiation light, magnification, focal length, and the like) by the endoscope 110, a drive instruction of the energy treatment tool, and the like via the input device 144.

The type of the input device 144 is not limited. The input device 144 may be, for example, a mouse, a keyboard, a touch panel, a switch, a lever (none of which are illustrated), a foot switch 144*a*, or the like. The touch panel is superimposed on a screen of the display device 149, for example, and the user can perform an input operation on a captured image of the endoscope 110 displayed on the screen, for example. Furthermore, as the input device 144, a head mounted display or various types of wearable devices may be used to input information according to the user's line-of-sight or gesture. Furthermore, the input device 144 may include a microphone that collects a voice of the user, and may input a voice command from the user. By using a device capable of inputting information in a non-contact manner for the input device 144, the user belonging to a clean area can operate a device belonging to an unclean area in a non-contact manner, and the user can input information without releasing his/her hand from the medical instruments 131, 132, . . . that he/she possesses.

The treatment tool control device 145 controls driving of an energy treatment tool for cauterization and incision of tissue, sealing of a blood vessel, and the like. For the purpose of securing a field of view by the endoscope 110 and securing a working space of the surgeon, the air film device 146 sends gas into a body cavity of the patient 103 through an undulating tube to inflate the body cavity. The recorder 147 includes, for example, a large-capacity recording device such as a solid state drive (SSD) or a hard disc drive (HDD), and is used for recording various types of information regarding surgery. The printer 148 is a device that prints data such as characters, images, and figures on paper, and is used to print information regarding surgery.

C. Camera Head and CCU

Figure 2:
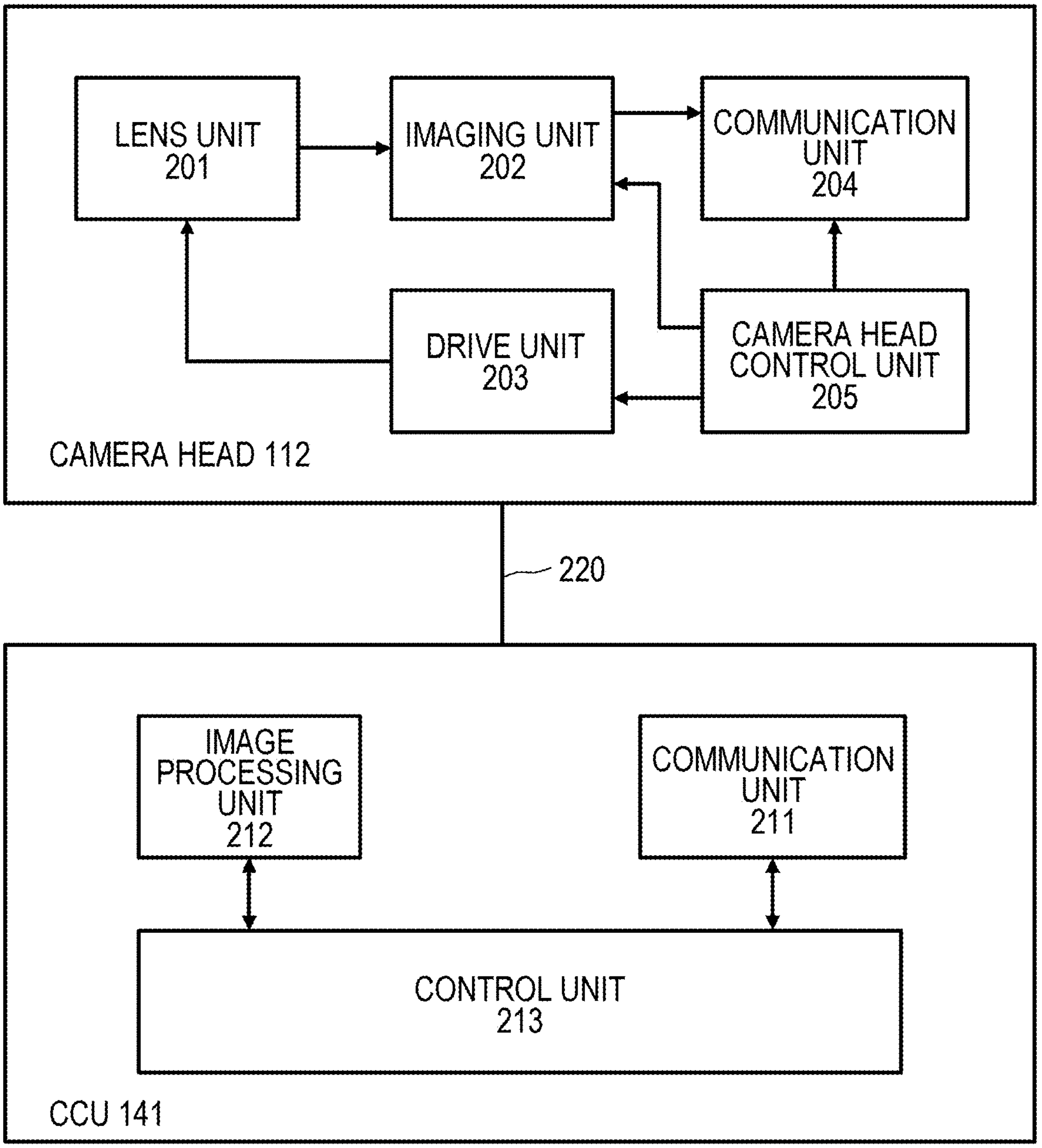
FIG. 2 is a diagram illustrating a functional configuration example of a camera head and a CCU.

FIG. 2 schematically illustrates a functional configuration example of the camera head 112 and the CCU 141. The camera head 112 includes a lens unit 201, an imaging unit 202, a drive unit 203, and a camera head control unit 205. Furthermore, the CCU 141 includes a communication unit 211, an image processing unit 212, and a control unit 213.

First, a functional configuration of the camera head 112 will be described. The lens unit 201 is an optical system disposed at a connection part with the lens barrel 111. Observation light taken in from a tip of the lens barrel 111 is guided to the camera head 112 and enters the lens unit 201. The lens unit 201 is configured by combining a plurality of optical lenses including a zoom lens and a focus lens. Optical characteristics of the lens unit 201 are adjusted such that incident light forms an image on a light receiving surface of an imaging element of the imaging unit 202. Furthermore, the zoom lens and the focus lens are movable in position on an optical axis in order to adjust the magnification and focus of a captured image.

The imaging unit 202 includes an imaging element including an image sensor such as a complementary semiconductor (CMOS), for example, and is disposed at a subsequent stage of the lens unit 201. The imaging unit 202 may be disposed immediately after an objective lens inside the lens barrel 111 instead of inside the camera head 112. The imaging unit 202 photoelectrically converts the observation light formed on the light receiving surface of the imaging element by the lens unit 201, generates an image signal corresponding to the observation image, and outputs the image signal to the communication unit 203.

For example, if a high-resolution image of the surgical site is obtained using an imaging element capable of coping with imaging of a high-resolution image of 4K or more, the surgeon 101 can grasp a state of the surgical site with a high-resolution image on the screen of the display device 149, and can more smoothly progress the surgery. Furthermore, the imaging unit 202 may include a pair of imaging elements so as to support 3D display. By performing the 3D display, the surgeon 101 can more accurately grasp the depth of the living tissue in the surgical site, and can more smoothly progress the surgery.

The drive unit 203 includes an actuator, and moves the zoom lens and the focus lens of the lens unit 201 by a predetermined distance in the optical axis direction under the control of the camera head control unit 205 to adjust the magnification and focus of an image captured by the imaging unit 202.

The communication unit 204 includes a communication device that transmits and receives various types of information to and from the CCU 141, and is mainly used to transmit an image signal obtained from the imaging unit 202 to the CCU 141 via a transmission cable 220. In order for the surgeon 101 to perform surgery more safely and reliably while observing the captured image of the affected part, it is necessary to display a moving image of the affected part in real time. Therefore, in order to transmit the image signal obtained from the imaging unit 202 with low latency, the communication unit 204 preferably performs optical communication. In a case of performing optical communication, the communication unit 204 includes an electro-optical conversion module, converts an electrical signal into an optical signal, and transmits the optical signal to the CCU 141 via the transmission cable (optical fiber) 220.

Furthermore, the communication unit 204 receives a control signal for controlling the drive of the camera head 112 from a side of the CCU 141, and supplies the control signal to the camera head control unit 205. The control signal includes information regarding a frame rate of the captured image, information regarding the exposure at the time of imaging, and information regarding the magnification and focus of the captured image. This control signal may also be transmitted by optical communication. In this case, the communication unit 204 includes a photoelectric conversion module, converts an optical signal received via the transmission cable 220 into an electric signal, and supplies the electric signal to the camera head control unit 205. Note that imaging conditions such as a frame rate, an exposure value, a magnification, and a focus are automatically set by the control unit 213 on the side of the CCU 141. That is, functions of auto exposure (AE), auto focus (AF), and auto white balance (AWB) are installed in the endoscope 110.

The camera head control unit 205 controls the drive of the camera head 112 on the basis of the control signal received from the CCU 141 via the communication unit 204. For example, the camera head control unit 205 controls the drive of the imaging element of the imaging unit 202 on the basis of the control signal that specifies a frame rate or an exposure value. Furthermore, the camera head control unit 205 adjusts positions of the zoom lens and the focus lens of the lens unit 201 in the optical axis direction via the drive unit 203 on the basis of the control signal for designating the magnification and the focus of the captured image. Furthermore, the camera head control unit 205 may have a function of storing information for identifying the lens barrel 111 and the camera head 112.

Note that by disposing a part of the camera head 112 such as the lens unit 201 and the imaging unit 202 in a sealed structure having high confidentiality and waterproofness, resistance to autoclave sterilization can be imparted.

Next, a functional configuration of the CCU 141 will be described. The communication unit 211 includes a communication device that transmits and receives various types of information to and from the camera head 112, and is mainly used for the camera head 112 to receive an image signal obtained from the imaging unit 202 via the transmission cable 220. In a case of performing optical communication, the communication unit 211 includes a photoelectric conversion module, converts a received optical signal into an electric signal, and supplies the electric signal to the image processing unit 212.

Furthermore, the communication unit 211 transmits a signal for controlling the drive of the camera head 112 to the camera head 112. The control signal includes information regarding the frame rate of the captured image, information regarding the exposure at the time of imaging, and information regarding the magnification and focus of the captured image (the same as above). This control signal may also be transmitted by optical communication. In this case, the communication unit 211 includes an electro-optical conversion module, converts an electric signal into an optical signal, and transmits the optical signal to the camera head 112 via the transmission cable 220.

The image processing unit 212 performs image processing on the image signal transmitted from the camera head 112. The image processing includes, for example, signal processing such as development processing, high image quality processing (band coordination processing, super-resolution processing, noise reduction (NR) processing, camera shake correction processing, and the like), and enlargement processing (electronic zoom processing). Furthermore, the image processing unit 212 performs detection processing on an image signal for performing AE, AF, and AWB.

The image processing unit 212 includes, for example, a processor such as a CPU and a GPU, a local memory thereof, and the like, and executes the above described image processing and detection processing by the processor executing a predetermined program loaded in the local memory. Furthermore, in a case where the image processing unit 212 includes a plurality of GPUs, information regarding an image signal may be appropriately divided, and image processing may be performed in parallel by the plurality of GPUs.

The control unit 213 performs various types of control related to imaging of the surgical site by the endoscope 110 and display of the captured image. For example, the control unit 213 generates a control signal for controlling the drive of the camera head 112. In a case where the user inputs the imaging conditions via the input device 144, the control unit 213 generates a control signal on the basis of the user input. Furthermore, in a case where the AE function, the AF function, and the AWB function are mounted on the endoscope 110, the control unit 213 calculates an optimum exposure value, focal length, and white balance on the basis of a result of the detection processing by the image processing unit 212, and generates a control signal.

Furthermore, the control unit 213 causes the display device 149 to display an image of the surgical site in the body cavity of the patient imaged by the endoscope 110 on the basis of the image signal subjected to the image processing by the image processing unit 212. The control unit 213 may superimpose and display surgery support information when displaying the image of the surgical site on the display device 149. The surgeon 101 can proceed with the surgery more safely and reliably on the basis of the surgery support information presented together with the image of the surgical site.

The transmission cable 220 connecting the camera head 112 and the CCU 141 may be an electric signal cable compatible with electric signal communication, an optical fiber compatible with optical communication, or a composite cable thereof. Alternatively, the camera head 112 and the CCU 141 may be wirelessly connected instead of a wired cable. In a case where the camera head 112 and the CCU 141 are connected by wireless communication, it is not necessary to lay the transmission cable 220 in an operating room, and movement of a medical staff such as the surgeon 101 and an assistant is not hindered by the transmission cable 220.

D. Regarding Endoscope

The lens barrel 111 of the endoscope 110 is assumed to be a rigid scope as an example. Examples of the type of the rigid endoscope include a forward-viewing endoscope in which an optical axis of the rigid endoscope coincides with an axial direction of the lens barrel (the lens faces a front direction), and an oblique-viewing endoscope in which the optical axis of the rigid endoscope is inclined with respect to the axis of the lens barrel.

Figure 3:
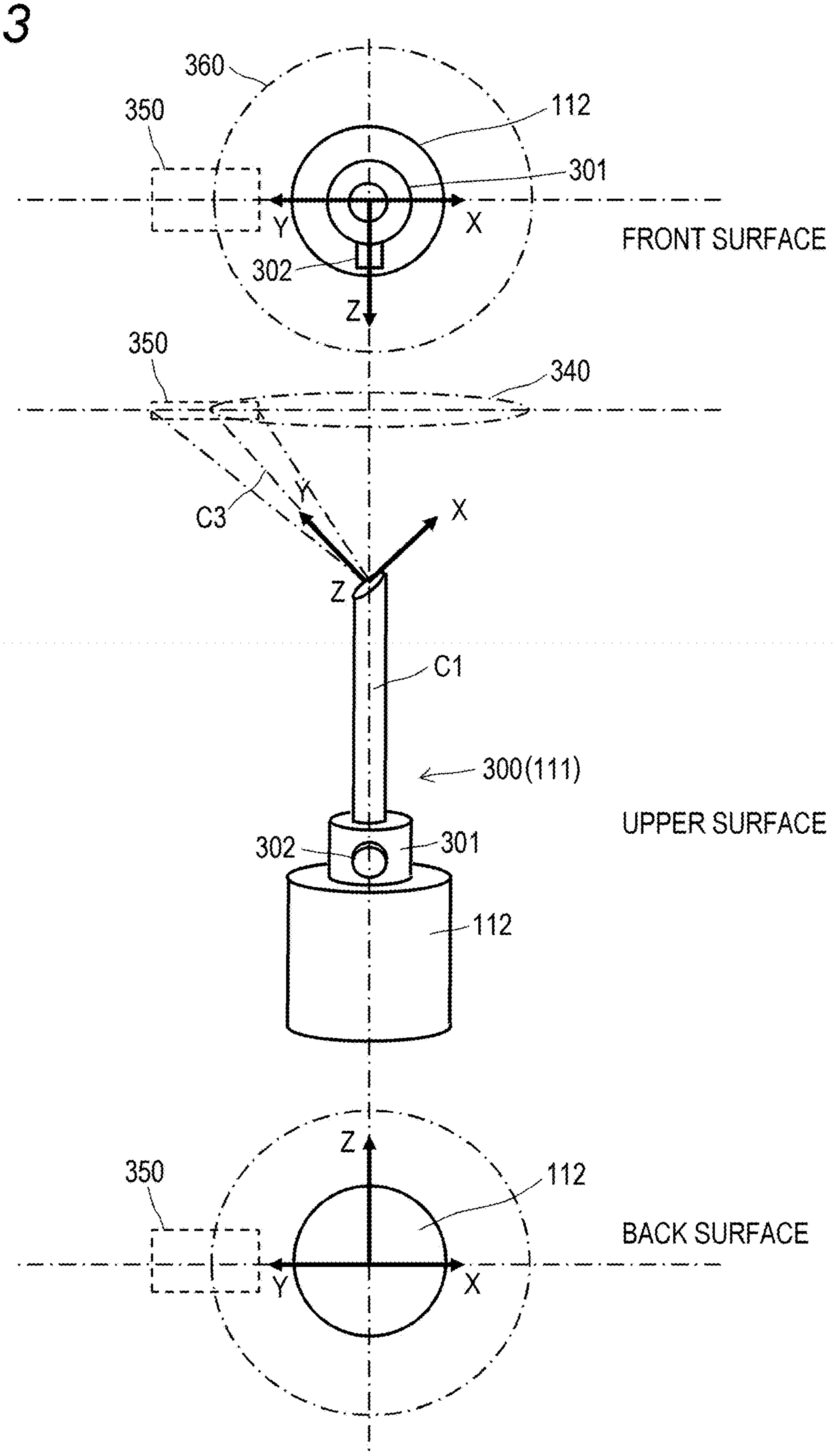
FIG. 3 is a diagram illustrating a positional relationship viewed from each of an upper surface and a front surface of an oblique-viewing endoscope 300, and a back surface side of a camera 200.

FIG. 3 schematically illustrates a positional relationship viewed from each of an upper surface and a front surface (a side of a target tissue) of an oblique-viewing endoscope 300 (the lens barrel 111 in a case of a rigid oblique-viewing endoscope), and a back surface side of a camera 200. The oblique-viewing endoscope 300 is attached to a tip of the camera head 112 via an eyepiece unit 301. The oblique-viewing endoscope 300 is optical-axis-rotatable independently of the camera head 112. Note that a light guide attached to a light guide connector 302 extends inside the oblique-viewing endoscope 300. Light generated by the light source device 142 such as an LED or a laser is guided to a tip of the oblique-viewing endoscope 300 by the light guide, and is emitted toward an observation target in the abdominal cavity of the patient via the objective lens.

The tip part of the medical arm device 120 has a structure in which orthogonal rotation axes with three degrees of freedom for determining an attitude of the oblique-viewing endoscope 300 are intensively disposed (not illustrated in FIG. 3). Here, the orthogonal rotation axes of three degrees of freedom have a structure in which a rotation axis around an optical axis C1 of the oblique-viewing endoscope 300, a left-right rotation axis, and a vertical rotation axis are disposed in order from the most tip part. A degree-of-freedom structure of the medical arm device 120 will be described later.

In FIG. 3, a plane that is perpendicular to the optical axis C1 of an eyepiece optical system and in which a target tissue is present is defined as an operative field plane 340. Then, a camera field-of-view range 350 corresponding to an imaging region of the imaging element in the camera head 112 exists on the operative field plane 340. Furthermore, an optical axis C3 of an objective optical system of the oblique-viewing endoscope 300 is inclined by a predetermined angle with respect to the optical axis C1 of the eyepiece optical system. When the most tip part of the medical arm device 120 rotates the oblique-viewing endoscope 300 around the optical axis C1 of the eyepiece optical system, the optical axis C3 of the objective optical system also rotates around the optical axis C1 of the eyepiece optical system, and a center of the camera field-of-view range 350 moves while drawing a rotational movement locus 360 on the operative field plane 340.

Figure 4:
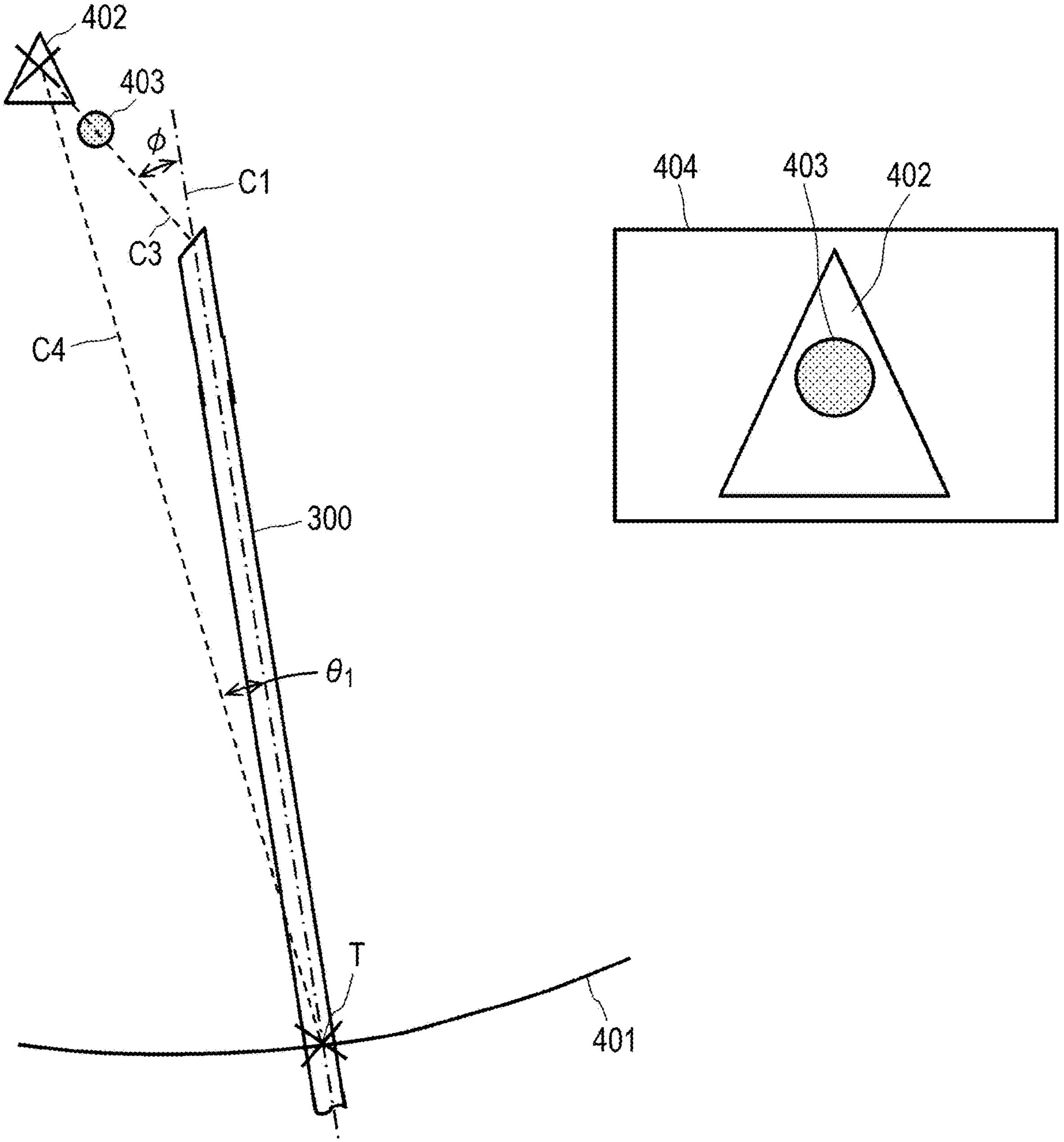
FIG. 4 is a diagram illustrating a state where the oblique-viewing endoscope 300 is inserted into an abdominal cavity from an abdominal wall 401 of a patient 103, and an observation target 402 such as an affected part is observed.

FIG. 4 illustrates a state where the oblique-viewing endoscope 300 is inserted into an abdominal cavity from an abdominal wall 401 of the patient 103 and an observation target 402 such as an affected part is observed. A trocar point T is a place where the trocar 151 is punctured into the abdominal wall 401, and corresponds to a position where the oblique-viewing endoscope 300 is inserted into the human body. A reference numeral 402 indicates an observation target by the oblique-viewing endoscope 300 (or the endoscope 1100), and a reference numeral 403 indicates an obstacle such as an organ. Furthermore, C4 is a direction connecting the trocar point T and the observation target 402. In the example illustrated in FIG. 4, the oblique-viewing endoscope 300 is inserted into the abdominal cavity in a direction inclined by an angle $\theta_1$ clockwise on the paper from C4.

The optical axis C1 of the eyepiece optical system of the oblique-viewing endoscope 300 can be rotated with the trocar point T as a fulcrum. Furthermore, the oblique-viewing endoscope 300 can be advanced and retracted into the abdominal cavity from the trocar point T. Therefore, the position and attitude of the oblique-viewing endoscope 300 can be changed by combining the rotation of the oblique-viewing endoscope 300 about the trocar point T as a fulcrum and the movement in an advancing and retracting direction. Furthermore, as described above, the optical axis C3 of the objective optical system at the tip of the oblique-viewing endoscope 300 is inclined by a predetermined angle φ with respect to the optical axis C1 of the eyepiece optical system (a longitudinal direction of the oblique-viewing endoscope 300). A direction of the optical axis C3 (that is, a line-of-sight direction of the endoscope 110) of the objective optical system can be changed by rotating the oblique-viewing endoscope 300 around the optical axis C1 of the eyepiece optical system. In short, the field-of-view range of the endoscope 110 can be changed by combining the rotation of the oblique-viewing endoscope 200 about the trocar point T as a fulcrum, the movement in the advancing and retracting direction, and the rotation of the oblique-viewing endoscope 200 around the optical axis C1 of the eyepiece optical system.

In the position and attitude of the oblique-viewing endoscope 300 illustrated in FIG. 4, the obstacle 403 exists between the tip of the oblique-viewing endoscope 300 and the observation target 402. Since the observation target 402 becomes a shadow of the obstacle 403, the entire region of the observation target 402 cannot be observed with the image imaged by the endoscope 110. A reference numeral 404 indicates an image captured by the endoscope 110 in this state.

Figure 5:
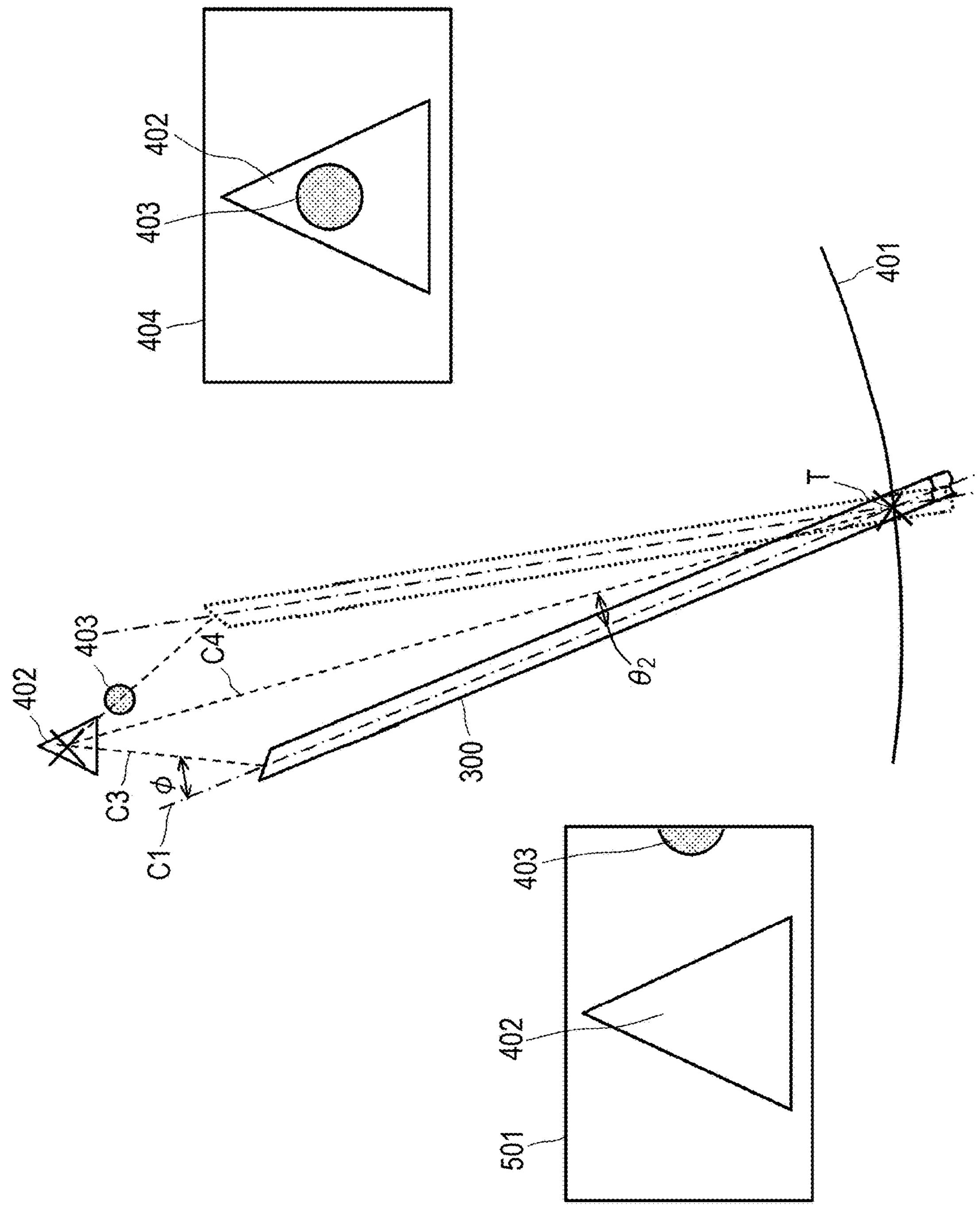
FIG. 5 is a diagram illustrating a state where the observation target 402 is observed while changing a position and an attitude of the oblique-viewing endoscope 300 inserted into the abdominal cavity.

FIG. 5 illustrates a state where the observation target 402 is observed by changing the position and attitude of the oblique-viewing endoscope 300 inserted into the abdominal cavity. The oblique-viewing endoscope 300 is rotated with the trocar point T as a fulcrum, and is inclined counterclockwise on the paper by an angle θ2 from the C4 direction connecting the trocar point T and the observation target 402. Furthermore, the oblique-viewing endoscope 300 is rotated around the optical axis of the eyepiece optical system to appropriately adjust an optical axis direction of the objective optical system. As illustrated in FIG. 5, in a state where the position, attitude, and line-of-sight direction of the oblique-viewing endoscope 300 are changed, the obstacle 403 is removed from between the objective lens at the tip of the oblique-viewing endoscope 300 and the observation target 402. Therefore, the entire region of the observation target 402 can be observed with the image imaged by the endoscope 110 without being blocked by the obstacle 403. A reference numeral 501 indicates an image captured by the endoscope 110 in this state.

Since the tip part of the medical arm device 120 has a structure in which orthogonal rotation axes of three degrees of freedom that determine the attitude of the oblique-viewing endoscope 300 are disposed, it is possible to realize the rotation of the oblique-viewing endoscope 300 around the optical axis C1 of the eyepiece optical system as illustrated in FIGS. 4 and 5, and the rotation of the oblique-viewing endoscope with the trocar point T as a fulcrum and the movement of the oblique-viewing endoscope in the advancing and retracting direction. In the present disclosure, as will be described later, since the orthogonal rotation axes of three degrees of freedom are intensively disposed, it is possible to reduce the space affected by the movement of the tip part and to suppress interference with the work space of the surgeon.

E. Medical Arm Device and Arm Control Device

Figure 6:
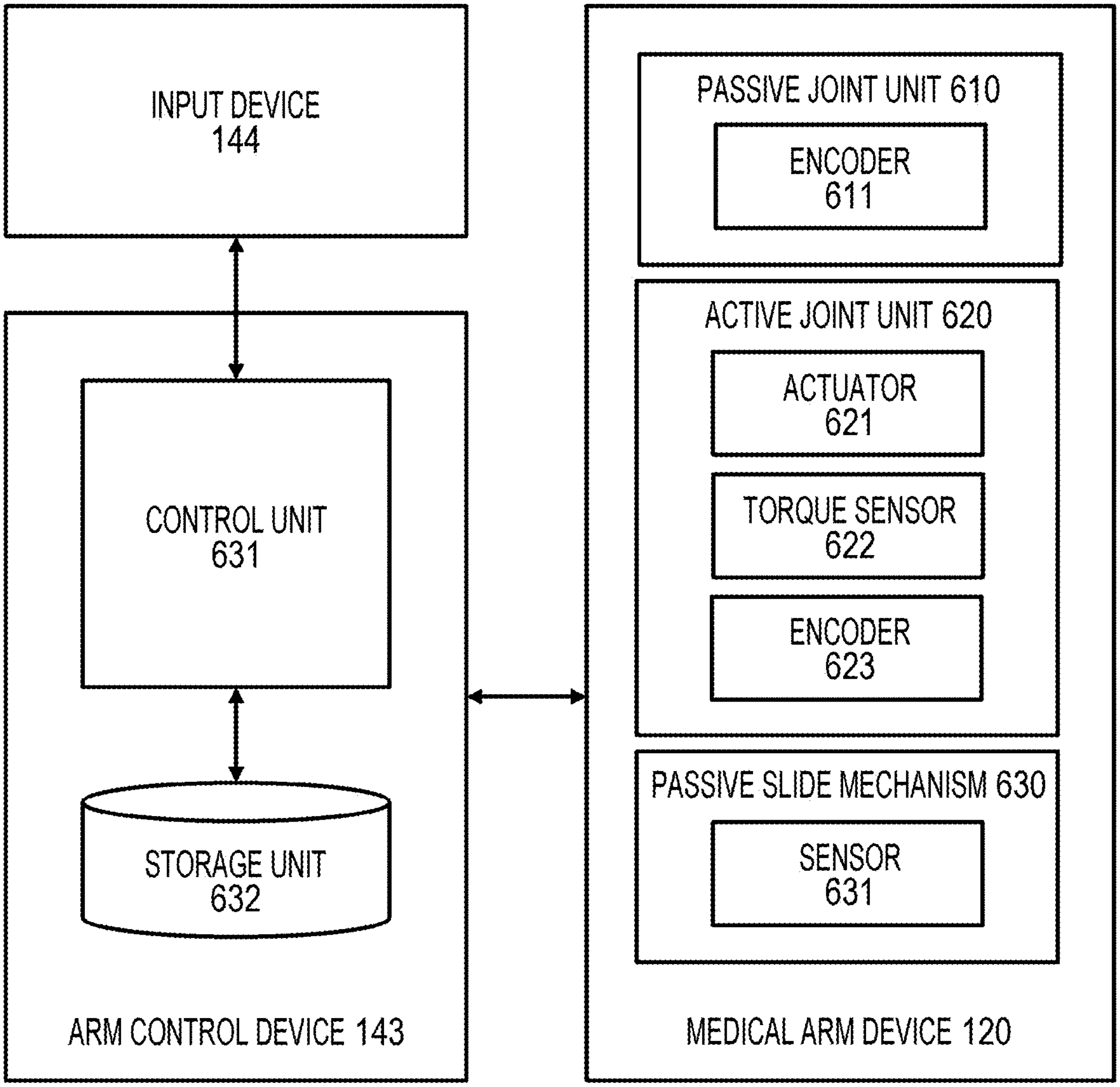
FIG. 6 is a diagram illustrating a functional configuration example of a medical arm device 120 and an arm control device 143.

FIG. 6 schematically illustrates a functional configuration example of the medical arm device 120 and the arm control device 143.

The medical arm device 120 is an arm including a multi-link structure having at least six degrees of freedom, and supports a medical instrument such as the endoscope 110 at a tip part. For example, a structure in which orthogonal rotation axes of three degrees of freedom for determining the attitude of the endoscope 110 are intensively disposed is provided. The structure in which the rotation axes are intensively disposed is a structure in which joint members corresponding to the rotation axes of three degrees of freedom are directly connected, or a structure in which a distance between a joint corresponding to the rotation axis around the longitudinal axis and a joint corresponding to the pitch axis has a distance that does not cause interference when rotating around the pitch axis. Furthermore, one of the six degrees of freedom is an inter-axis distance changing unit that adjusts a distance between two horizontal rotation axes of the second arm part of the arm. Details of the mechanical configuration of the medical arm device 120 will be described later. In the functional configuration illustrated in FIG. 6, it is assumed that a function of the medical arm device 120 is abstracted, joints connecting the links are classified into two types of a passive joint unit 610 and an active joint unit 620, and the inter-axis distance changing unit is configured by a passive slide mechanism 630.

The passive joint unit 610 includes an encoder 611 that measures a joint angle. Furthermore, the active joint unit 620 includes an actuator 621 that rotationally drives the joint and an encoder 623 that measures a rotation angle of the joint. Moreover, a torque sensor 622 that detects torque acting on the joint may be provided. Furthermore, the passive slide mechanism 630 may include a sensor 631 that measures a slide amount, that is, an amount of change in the inter-axis distance.

The arm control device 143 controls the drive of the medical arm device 120 according to a predetermined control method such as position control or force control on the basis of a user's instruction input via the input device 144. Specifically, the arm control device 143 calculates a control amount of the actuator 621 of the active joint unit 620 according to a predetermined control method and supplies a drive signal. The arm control device 143 includes a control unit 631 and a storage unit 632. The control unit 631 includes, for example, a processor such as a CPU and a local memory thereof, and executes a predetermined program loaded from the storage unit 632 or the like into the local memory by the processor. The storage unit 632 is, for example, a mass storage device such as an SSD or an HDD, and stores data such as a program code executed by the control unit 631 and a robot model used during program execution in a file format.

The control unit 631 may generate control information of the medical arm device 120 using a learned neural network model so as to predict the motion of the medical arm device 120 by deep learning or the like. For example, the control unit 631 may generate a target command value of the medical arm device 120 on the basis of environment recognition information and instrument recognition information generated by a neural network model for image recognition used by the control unit 213 in the CCU 141.

Note that the neural network model for motion prediction used by the control unit 631 may also generate a command value (imaging conditions such as a frame rate, an exposure value, a magnification, and a focus) for the endoscope 110 supported at the tip by the medical arm device 120 together with a command value for the medical arm device 120. Furthermore, the neural network model for image recognition used by the control unit 213 in the CCU 141, and the neural network model for motion prediction used by the control unit 631 in the arm control device 143 may be integrated into one to be configured as an End to End (E2E) neural network model.

The arm control device 143 and the medical arm device 120 may be an electric signal cable compatible with electric signal communication, an optical fiber compatible with optical communication, or a composite cable thereof. Furthermore, it may be included in the above described transmission cable 220. Furthermore, the arm control device 143 and the medical arm device 120 may be wirelessly connected instead of a wired cable.

F. Configuration of Medical Arm Device

The medical arm device 120 according to the present embodiment satisfies the following three requirements, suppresses an increase in size of the device, and realizes a medical arm device that realizes a higher degree of freedom of the arm and a wider movable range.

(1) Capable of controlling an attitude of an endoscope with six degrees of freedom or more (2) Ensure a sufficient operating range of the endoscope during surgery (3) Correspond to various procedures The medical arm device 120 has a degree-of-freedom structure capable of avoiding interference with the surgeon in order to realize smooth cooperative work with the surgeon during surgery after satisfying the three requirements described above.

F-1. Overall Configuration

Figure 7:
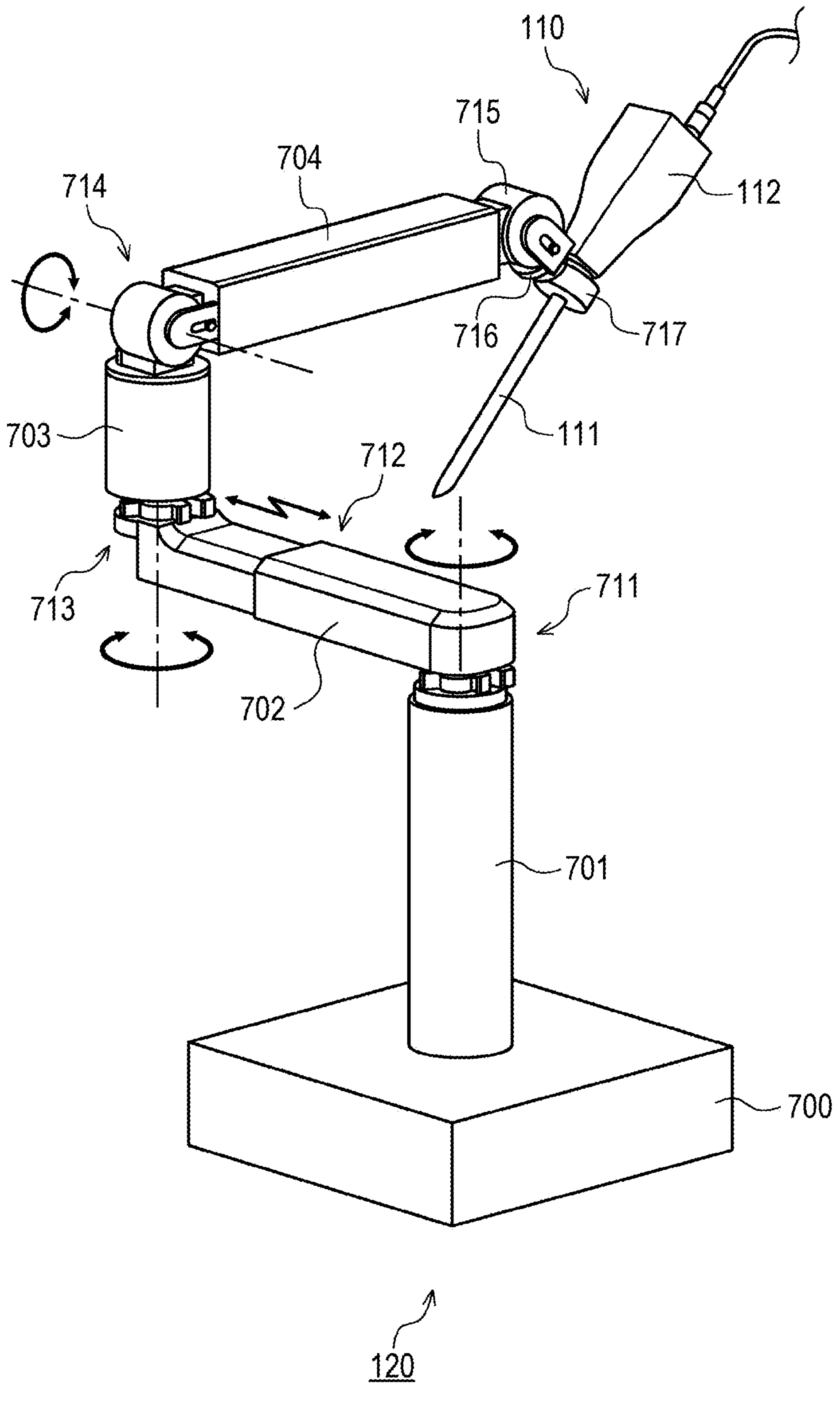
FIG. 7 is a diagram illustrating an appearance configuration example of the medical arm device 120.

FIG. 7 illustrates an appearance configuration example of the medical arm device 120 applied to the endoscopic surgery system 100. The illustrated medical arm device 120 is an arm including a multi-link structure having 7 degrees of freedom, supports the endoscope 110 at the tip part, and has a structure in which orthogonal rotation axes of 3 degrees of freedom for determining the attitude of the endoscope 110 are intensively disposed. Furthermore, the remaining six degrees of freedom include three degrees of freedom of two horizontal rotation axes and an inter-axis distance changing unit that adjusts a distance between these horizontal rotation axes.

Specifically, the medical arm device 120 includes a base part 700, a first link 701 attached substantially vertically to the base part 700, a first joint part 711 having a degree of freedom around a horizontal rotation axis (alternatively, a longitudinal axis of the first link 701) at a tip of the first link 701, a second link 702 attached in a horizontal direction to the tip of the first link 701 via the first joint part 711 and including a slide mechanism 712 extending and contracting in a longitudinal direction, a second joint part 713 having a degree of freedom around the horizontal rotation axis (or an axis orthogonal to a longitudinal axis of the second link 702.) at a tip of the second link 702, a third link 703 attached substantially vertically to the tip of the second link 702 via the second joint part 713, a third joint part 714 having a degree of freedom around a vertical rotation axis (or an axis orthogonal to a longitudinal axis of the third link 703) orthogonal to the horizontal rotation axis at a tip of the third link 703, a fourth link 704 attached to a tip of the third link 703 via the third joint part 714, and a tip part supporting the endoscope 110 at a tip of the fourth link 704.

Here, the second link 702 expands and contracts in the longitudinal direction by the slide mechanism 712, so that a distance between the first joint part 711 and the second joint part 712 having the degree of freedom around the horizontal rotation axis can be changed.

Furthermore, the base part 700 has a structure (not illustrated) attached to a frame of the surgical bed 102, for example. Of course, the base part 700 may be installed on a floor surface of an operating room or may be installed on a ceiling.

The tip part supporting the endoscope 110 at a distal end of the fourth link 704 has a structure in which orthogonal rotation axes of three degrees of freedom for determining an attitude of the endoscope 110 are intensively disposed. Therefore, the medical arm device 120 has a total of seven degrees of freedom, and can control the attitude of the endoscope 110 with seven degrees of freedom. The structure in which the orthogonal rotation axes of three degrees of freedom of the tip part are intensively disposed corresponds to, for example, a structure in which three orthogonal rotation axes are connected without interposing a link, or a structure in which joint members corresponding to the three rotation axes are directly connected, and more specifically, a member connecting the three joint parts is not a link that gains an arm length but only a component that connects the joint parts. Note that the tip part that supports the endoscope 110 and the fourth link 704 having the tip part are referred to as a first arm part. Furthermore, a link part (the first link 701 and the second link) including two horizontal rotation axes (the first joint part 711 and the second joint part 713) and an inter-axis distance changing unit (the slide mechanism 712) is defined as a second arm part. In the medical arm device 120 illustrated in FIG. 7, the second arm part is connected by the third joint part 714 having a degree of freedom around the vertical rotation axis.

Figure 8:
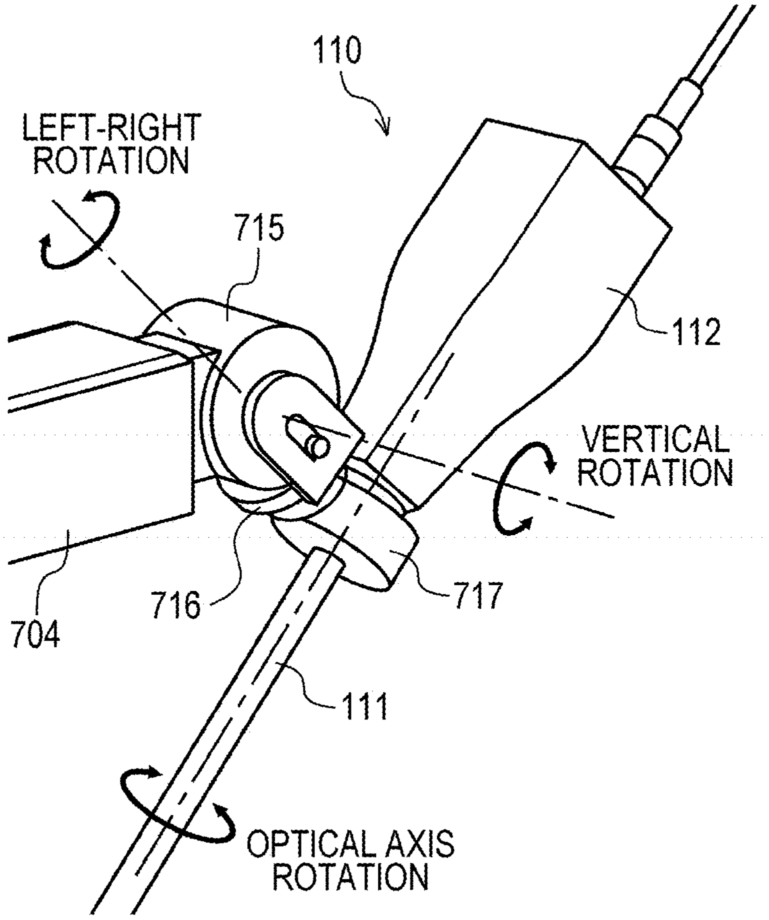
FIG. 8 is an enlarged view illustrating a structure of a tip part that supports the endoscope 110.

FIG. 8 illustrates an enlarged structure of the tip part that supports the endoscope 110. The tip part may support a medical instrument other than the endoscope 110. As illustrated in FIG. 8, the tip part includes a vertical rotation axis part 715 having a degree of freedom around a vertical rotation axis (or an axis orthogonal to the longitudinal axis of the fourth link 704) of the tip of the fourth link 704 and swinging the endoscope 110 in the vertical direction, a left-right rotation axis part 716 adjacent to the vertical rotation axis part 715, having a degree of freedom around a left-right rotation axis orthogonal to the vertical rotation axis and swinging the endoscope 110 in the left-right direction, and an optical axis rotation axis part 717 having a degree of freedom around an optical axis of the endoscope 110 (lens barrel 111). Therefore, the orthogonal rotation axes of three degrees of freedom that determine the attitude of the endoscope 110 have a structure in which the optical axis rotation axis, the left-right rotation axis, and the vertical rotation axis of the endoscope 110 are disposed in this order from the most tip part. Note that the left-right rotation axis part 716 can be referred to as a pan axis that changes the observation direction of the endoscope 110, and the vertical rotation axis part 715 can be referred to as a tilt axis. Alternatively, in a case where the optical axis rotation axis part 717 is a roll axis, the left-right rotation axis part 716 can be referred to as a yaw axis, and the vertical rotation axis part 715 can be referred to as a pitch axis. If a combined volume of the joint parts corresponding to these three axes is smaller than a combined volume of the human wrist and hand, there is an advantage of using the medical arm device 120 instead of the scopist. The optical axis rotation axis part 717 desirably minimizes a length to grip the endoscope 110 in the axial direction so as not to reduce an effective length of the endoscope 110. Furthermore, a distance between the vertical rotation axis part 715 and the optical axis rotation axis part 717 is desirably set to a length that avoids self-interference of the arm. The structure in which the rotation axes orthogonal to each other with three degrees of freedom are intensively disposed as illustrated in FIG. 8 is a structure in which the joint members corresponding to the rotation axes with three degrees of freedom are directly connected, or a structure in which a distance between the joint corresponding to the rotation axis around the longitudinal axis and the joint corresponding to the pitch axis has a distance that does not cause interference when rotating around the pitch axis. Therefore, it is possible to reduce the space affected by the movement of the tip part, and it is possible to suppress interference with the work space of the surgeon. Incidentally, in a case where the vertical rotation axis part 715 is disposed closer to the root side, it is assumed that the movement on the surgeon's hand side becomes large when the vertical rotation axis part 715 is operated.

F-2. Regarding Response to Surgical Method

Figure 9:
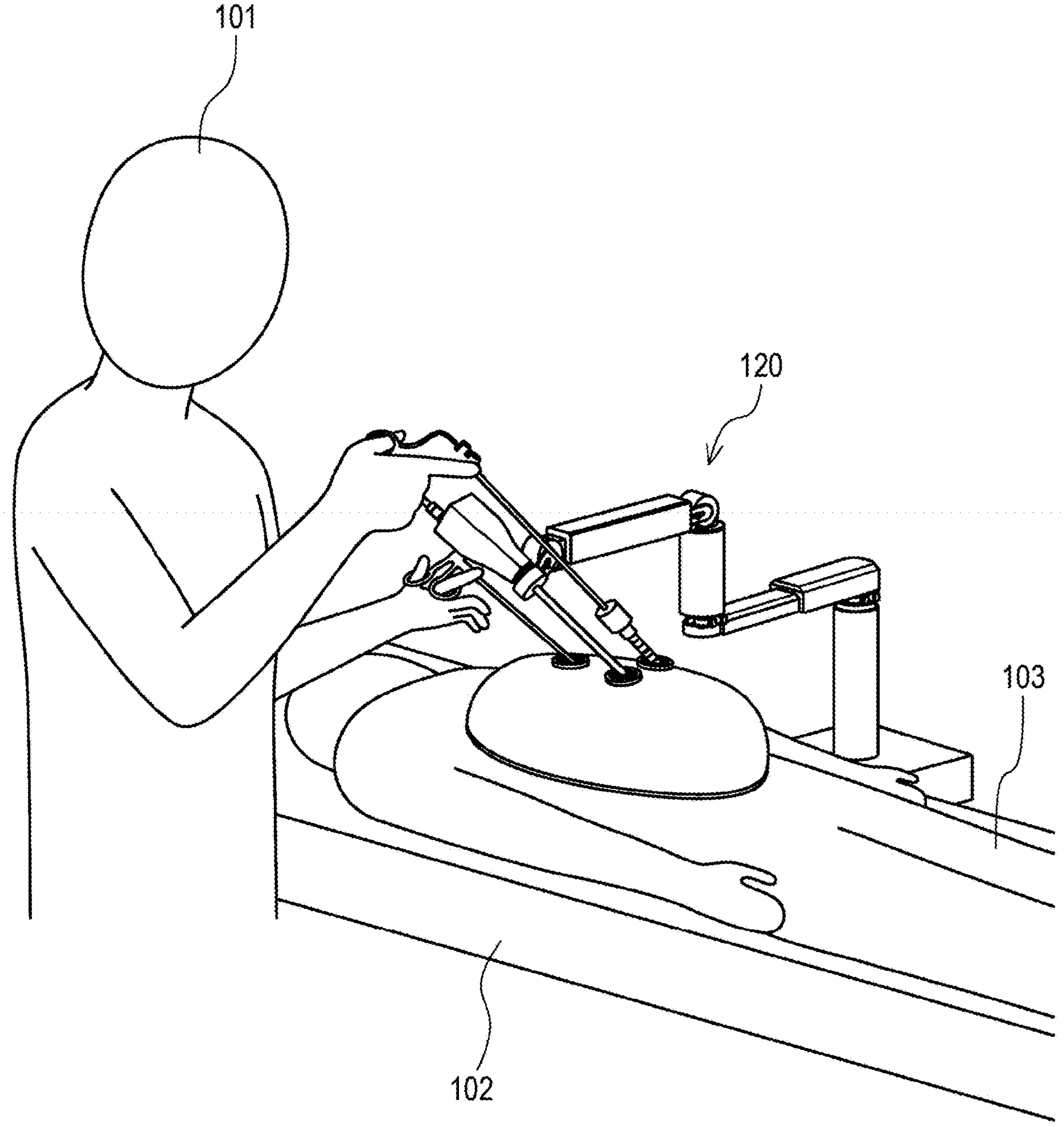
FIG. 9 is a diagram illustrating a surgical method in which the medical arm device 120 accesses between both hands of a surgeon 101 from a front of the surgeon 101.
Figure 10:
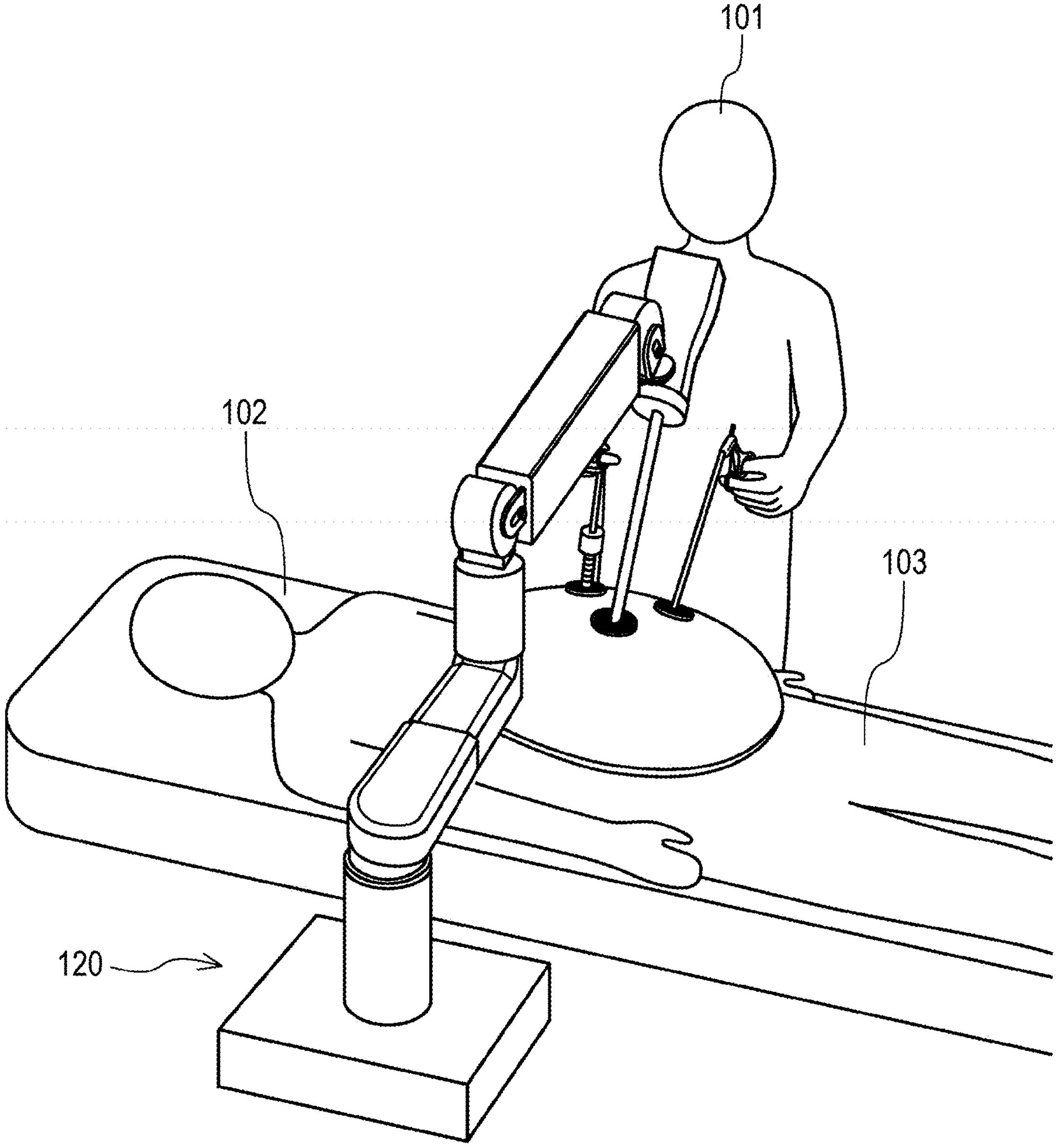
FIG. 10 is a diagram illustrating a surgical method in which the medical arm device 120 accesses between both hands of the surgeon 101 from a front of the surgeon 101.

As described above, the medical arm device 120 includes, in the second arm part on the root side, a three-degree-of-freedom structure including the first joint part 711 and the second joint part 713 each having a degree of freedom around the horizontal rotation axis, and the slide mechanism 712 capable of changing the distance between the first joint part 711 and the second joint part 713. Therefore, by adjusting the position and the direction in which the arm accesses the hand of the surgeon 101 by utilizing the three degrees of freedom of the second arm part, it is possible to avoid interference with the surgeon 101, an assistant, and other equipment in response to various surgical methods (change in installation position of arm and port position). FIGS. 9 and 10 illustrate surgical methods in which the medical arm device 120 accesses between both hands of the surgeon 101 from the front of the surgeon 101.

F-3. Structure of Root Part

Figure 11:
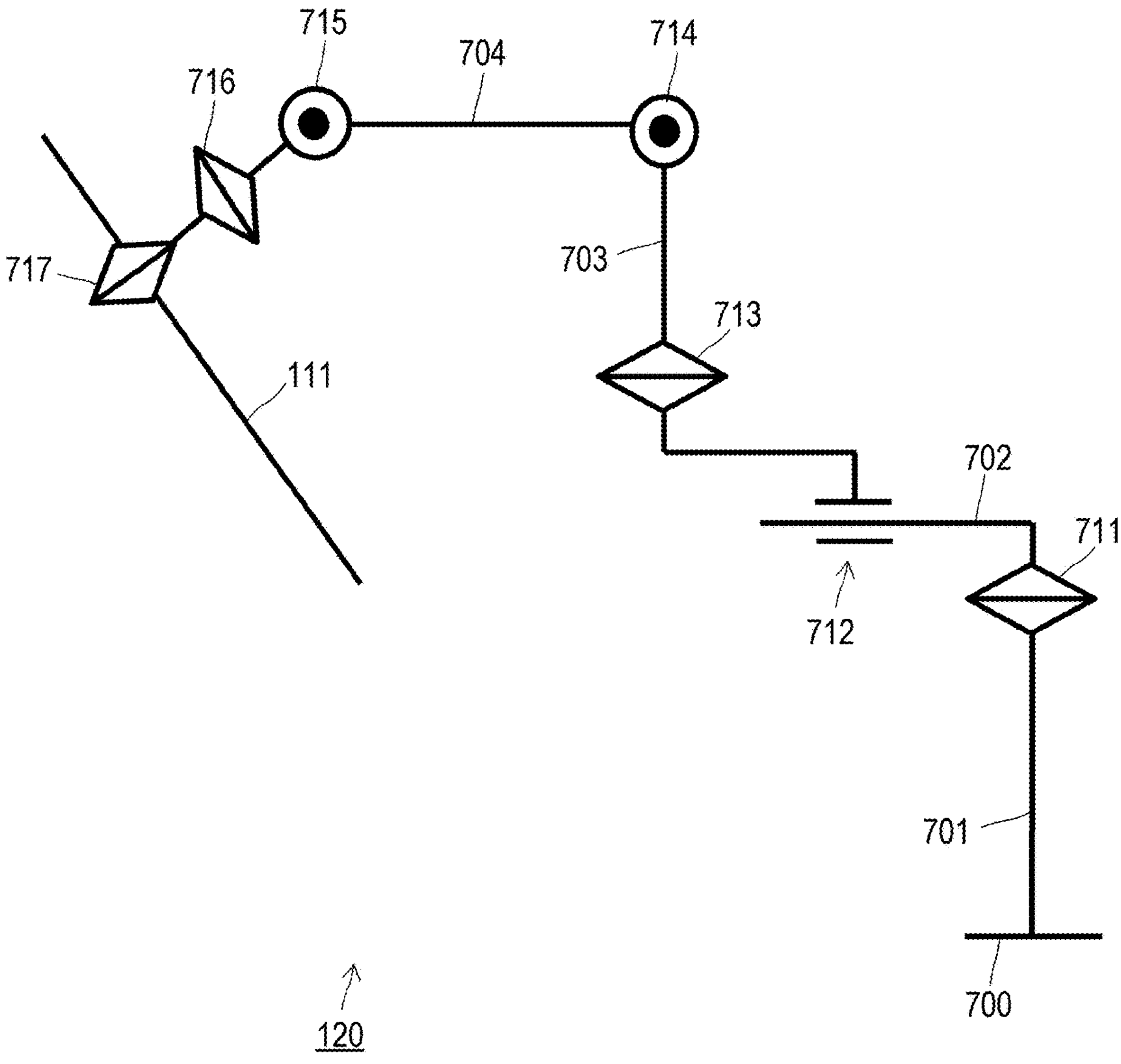
FIG. 11 is a diagram illustrating a degree-of-freedom configuration of the medical arm device 120.

FIG. 11 illustrates a degree-of-freedom configuration of the medical arm device 120 illustrated in FIG. 7. As described above, the medical arm device 120 includes the base part 700, the first link 701 attached substantially vertically to the base part 700, the first joint part 711 having a degree of freedom around the horizontal rotation axis at the tip of the first link 701, the second link 702 attached to the tip of the first link 701 via the first joint part 711 and including the slide mechanism 712 extending and contracting in the longitudinal direction, the second joint part 713 having a degree of freedom around the horizontal rotation axis at the tip of the second link 702, the third link 703 attached substantially vertically to the tip of the second link 702 via the second joint part 713, the third joint part 714 having a degree of freedom around the vertical rotation axis orthogonal to the horizontal rotation axis at the tip of the third link 703, a fourth link 704 attached to the tip of the third link 703 via the third joint part 714, and the tip part supporting the endoscope 110 at the tip of the fourth link 704.

By extending the arm from the tip of the third degree of freedom of the second arm part on the root side, a reach range of the endoscope 110 at the tip can be expanded even if the fourth link 704 is short. In other words, since a link length of the fourth link 704 can be shortened, the load torque acting on the third joint part 714 at a root of the fourth link 704 can be reduced. Since an output of the actuator that drives the third joint part 714 can be reduced, space saving and weight reduction of the entire medical arm device 120 can be realized by downsizing of the actuator.

F-4. Regarding Support Mechanism of Tip Part

The first arm part having the tip part that supports the endoscope 110 at the distal end of the medical arm device 120 has a structure in which orthogonal rotation axes of three degrees of freedom that determine the attitude of the endoscope 110 are intensively disposed. As illustrated in FIG. 8, the tip part includes the vertical rotation axis part 715 having a degree of freedom around the vertical rotation axis at the tip of the fourth link 704, the left-right rotation axis part 716 adjacent to the vertical rotation axis part 715 and having a degree of freedom around the left-right rotation axis orthogonal to the vertical rotation axis, and the optical axis rotation axis part 717 having a degree of freedom around the optical axis of the endoscope 110 (lens barrel 111). In this manner, it is possible to realize downsizing of the tip part by intensively disposing the orthogonal rotation axes of three degrees of freedom that determine the attitude of the endoscope 110. In a case where the tip part is downsized, as can be seen from FIGS. 9 and 10, it is possible to avoid interference by suppressing the entry to the work space at hand of the surgeon 101 as much as possible. That is, by configuring the tip part to be connected with the rotation axis not via the link, it is possible to reduce the work space of the tip part when the tip part rotates and to avoid interference.

Furthermore, as can be seen from FIGS. 7, 8, and 11, the orthogonal rotation axes of three degrees of freedom that determine the attitude of the endoscope 110 have a structure in which the optical axis rotation axis, the left-right rotation axis, and the vertical rotation axis of the endoscope 110 are disposed in this order from the most tip part. As described with reference to FIGS. 3 to 5, the three degrees of freedom for determining the attitude of the endoscope 110 are necessary. It is necessary that the optical axis rotation axis part 717 that rotates the optical axis of the lens barrel 111 (oblique-viewing endoscope 300) is disposed at the most tip part. Furthermore, by disposing the left-right rotation axis part 716 on the second axis from the tip, the movement of the tip part at the time of an attitude change to the left and right is minimized, and interference between the hand or arm of the surgeon 101 and the tip part of the arm can be avoided.

F-5. Regarding Joint of Root Part

As illustrated in FIGS. 7, 8, and 11, the medical arm device 120 is an arm including a multi-link structure having at least six degrees of freedom, and includes the first arm part having the tip part with three degrees of freedom for determining the attitude of the endoscope 110, the two horizontal rotation axes (the first joint part 711 and the second joint part 713) in the second arm part on the root side, and the inter-axis distance changing unit (the slide mechanism 712) for changing the distance between the horizontal rotation axes. The slide mechanism 712 may be provided with an actuator for sliding the second link 702, and a length of the second link 702 can be adjusted by an operation by a user (such as the surgeon 101). Furthermore, at least one of the three degree-of-freedom mechanisms including the first joint part 711, the slide mechanism 712, and the second joint part 713 of the second arm part may be a passive mechanism that does not actively operate by the actuator. For example, the slide mechanism 712 provided in the second link 702 may be a passive slide mechanism. By using at least one degree of freedom of the second arm part as a passive mechanism, the weight of the entire medical arm device 120 can be reduced.

For example, the surgeon 101 or the assistant grips the third link 703 and pulls the third link from the root side in the horizontal direction or pushes the third link to the root side, so that the passive slide mechanism 712 contracts and the distance between the first joint part 711 and the second joint part 713, which are two horizontal rotation axes, can be changed. The surgeon 101 and the assistant can manually adjust the length of the second link 702 using the slide mechanism 712 according to a direction in which the medical arm device 120 accesses the hand of the surgeon 101 and the like, and can avoid interference between the hand or arm of the surgeon 101 and the tip part of the arm.

G. Modification Examples

G-1. Modification Examples of Root Part

Figure 12:
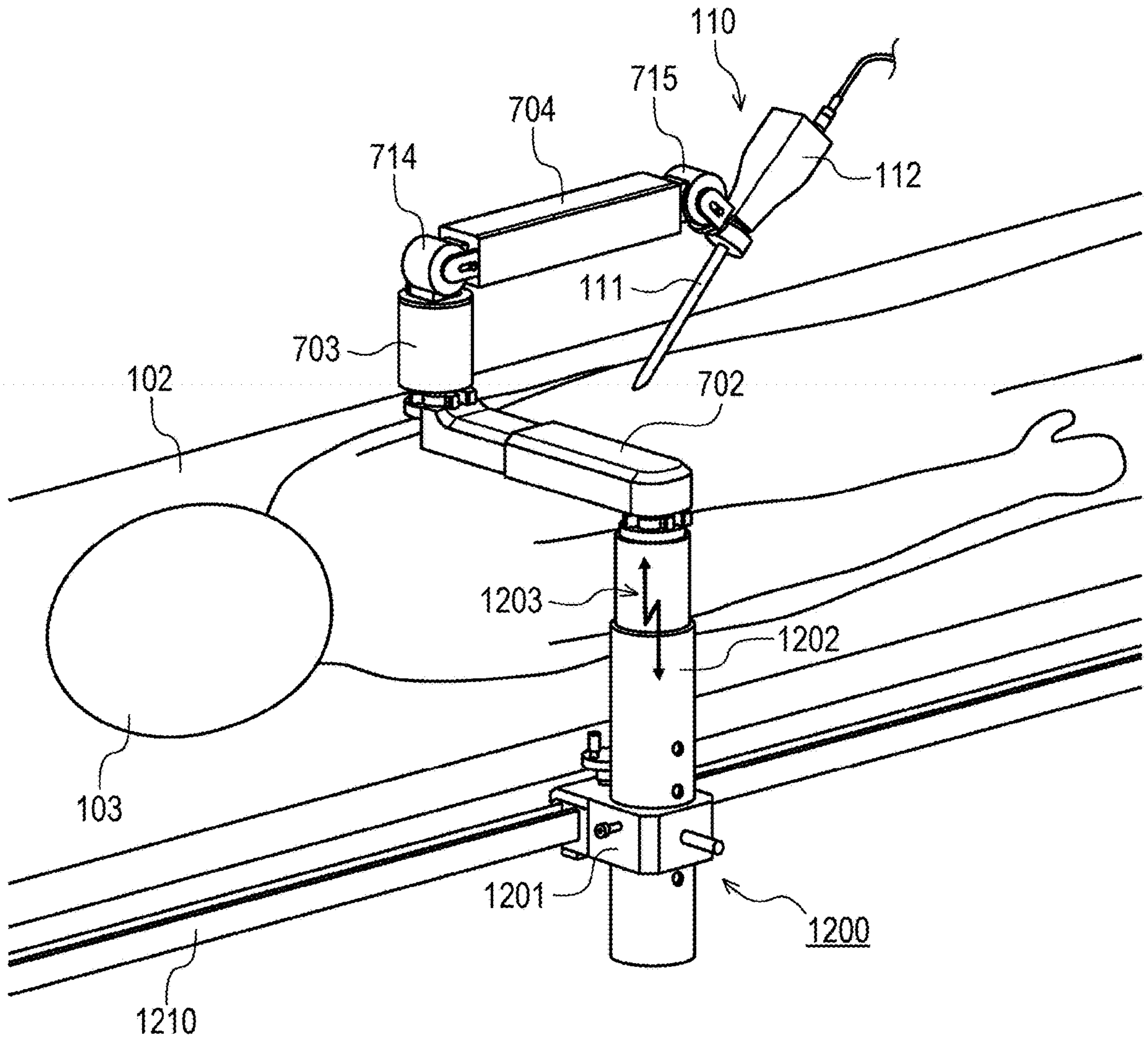
FIG. 12 is a diagram illustrating an appearance configuration example of a medical arm device 1200.
Figure 13:
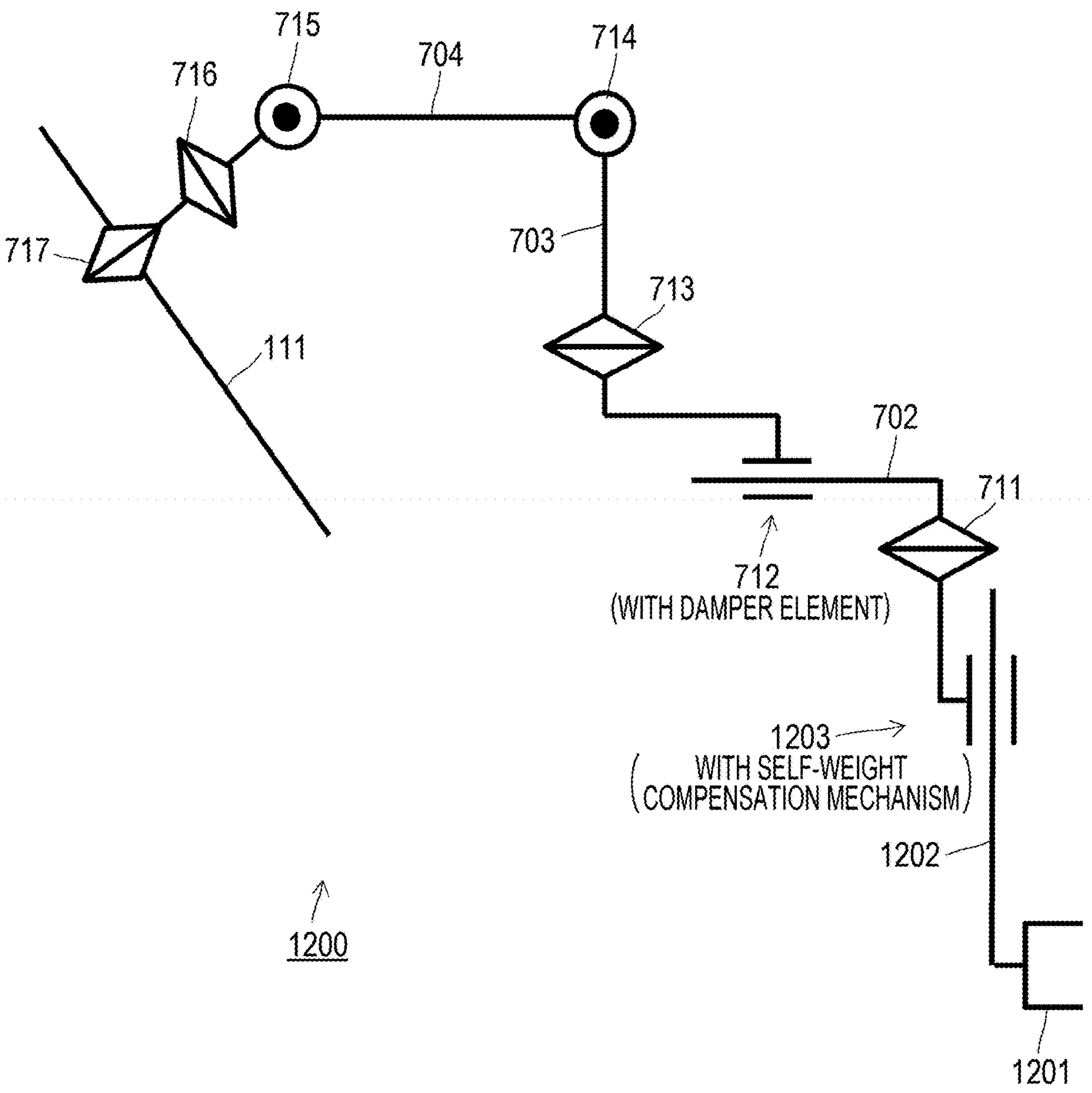
FIG. 13 is a diagram illustrating a degree-of-freedom configuration of the medical arm device 1200.

FIG. 12 illustrates an appearance configuration example of a medical arm device 1200 according to a modification example. Furthermore, FIG. 13 illustrates a degree-of-freedom configuration of the medical arm device 1200. The medical arm device 1200 illustrated in FIGS. 12 and 13 is mainly characterized in that it includes an attachment structure part 1201 attached to a bed rail 1210 provided along a length direction on a side part of the surgical bed 102, and that it includes a lifting-lowering mechanism 1203 in which a linear motion axis operable in a vertical direction is disposed on a first link 1202 on a root side to adjust a height on a tip side. The tip side of the first joint part 711 has the same configuration as the medical arm device 120 illustrated in FIGS. 7 and 11, and the corresponding components are denoted by the same reference numerals.

By moving and fixing the attachment structure part 1201 along the bed rail 1210, an arrangement position of the medical arm device 1200 can be adjusted according to an affected part position of the patient 103. Furthermore, the medical arm device 1200 is fixed to the surgical bed 102 at a position where the attachment structure part 1201 is attached to the bed rail 1210. Therefore, when the inclination of the surgical bed 102 is adjusted during surgery, a relative positional relationship between the patient 103 and the medical arm device 1200 can be maintained. During surgery, the surgical bed 102 may be inclined by, for example, about 30 degrees, but even in such a case, the medical arm device 120 according to the present disclosure can be used. Note that the medical arm device 1200 can access a free space at hand of the surgeon from an opposite side of the surgeon across the patient (or the surgical bed). In this manner, it is possible to avoid interference between the surgeon's hand or arm and the arm tip part by access from the surgeon's face.

Furthermore, the height of the tip side can be adjusted using the lifting-lowering mechanism 1203 including the linear motion axis for the first link 1202. For example, the height of the tip side can be adjusted using the lifting-lowering mechanism 1203 according to the physique of the patient 103, the position at which the endoscope 110 is inserted and removed, and the like.

The lifting-lowering mechanism 1203 of the first link 1202 may have a passive axis configuration without a driving actuator. Self-weight on the tip side of the first link 1202 acts on the passive axis. A self-weight compensation mechanism that compensates for the self-weight may be incorporated in the passive axis so that the lifting-lowering mechanism 1203 does not lower due to the self-weight. The self-weight compensation mechanism may include, for example, a hydraulic pressure, an air spring, a compression coil spring, a tension coil spring, or a combination of two or more thereof.

The surgeon 101 or the assistant can adjust the height of the endoscope 110 at the tip according to the physique of the patient 103 by, for example, gripping the second link and lifting or pushing the second link upward or downward from the root side to move the lifting-lowering mechanism 1203 of the first link 1202 up and down. Furthermore, since the self-weight compensation mechanism is incorporated in the lifting-lowering mechanism 1203, it is possible to perform an operation of lifting and lowering the first link 1202 with a low load without supporting the entire weight on the tip side of the first link 1202.

Note that the lifting-lowering mechanism of the first link 1202 can be configured by an active axis using a driving actuator. In this case, the driving actuator moves the lifting-lowering mechanism 1203 of the first link 1202 up and down according to the user's operation, and the height of the endoscope 110 at the tip can be adjusted according to the physique of the patient 103.

G-2. Modification Example of Slide Mechanism

The slide mechanism 712 provided in the second link 702 includes a passive slide mechanism (described above). Since the surgical bed 102 to which the medical arm device 1200 is attached is in the substantially horizontal direction, the self-weight on the tip side of the second joint part 713 does not act on the slide mechanism 712. However, when the surgical bed 102 is tilted or the like, there is a possibility that the self-weight of the tip side relative to the second joint part 713 acts on the slide mechanism 712 to cause a steep operation such as expansion and contraction of the second link 702. Such an operation may be transmitted to the endoscope 110 inserted into the abdominal cavity to damage the affected part.

Therefore, it is preferable to incorporate a damper element such as an oil damper in the passive slide mechanism 712 to suppress the steep operation. The damper element may have, for example, a structure in which a pressure is applied using a spring, a structure in which a frictional force due to contact between structure bodies is used, or the like.

G-3. Regarding Arrangement of Active Joints

Similarly, in the medical arm device 120 illustrated in FIGS. 7 and 11, as described in section G-2 described above, the slide mechanism 712 that adjusts the inter-axis distance between the first joint part 711 and the second joint part 713 on the root side both having the horizontal rotation axis may be a passive slide mechanism.

The medical arm device 120 includes a total of six rotation axes including the first joint part 711, the second joint part 713, the third joint part 714, the vertical rotation axis part 715, the horizontal rotation axis part 716, and the optical axis rotation axis part 717. So far, it has not been described whether these rotation axes are active axes driven by a motor or passive axes without an actuator such as a motor. All the rotation axes may be active axes, but some may be passive axes.

Figure 14:
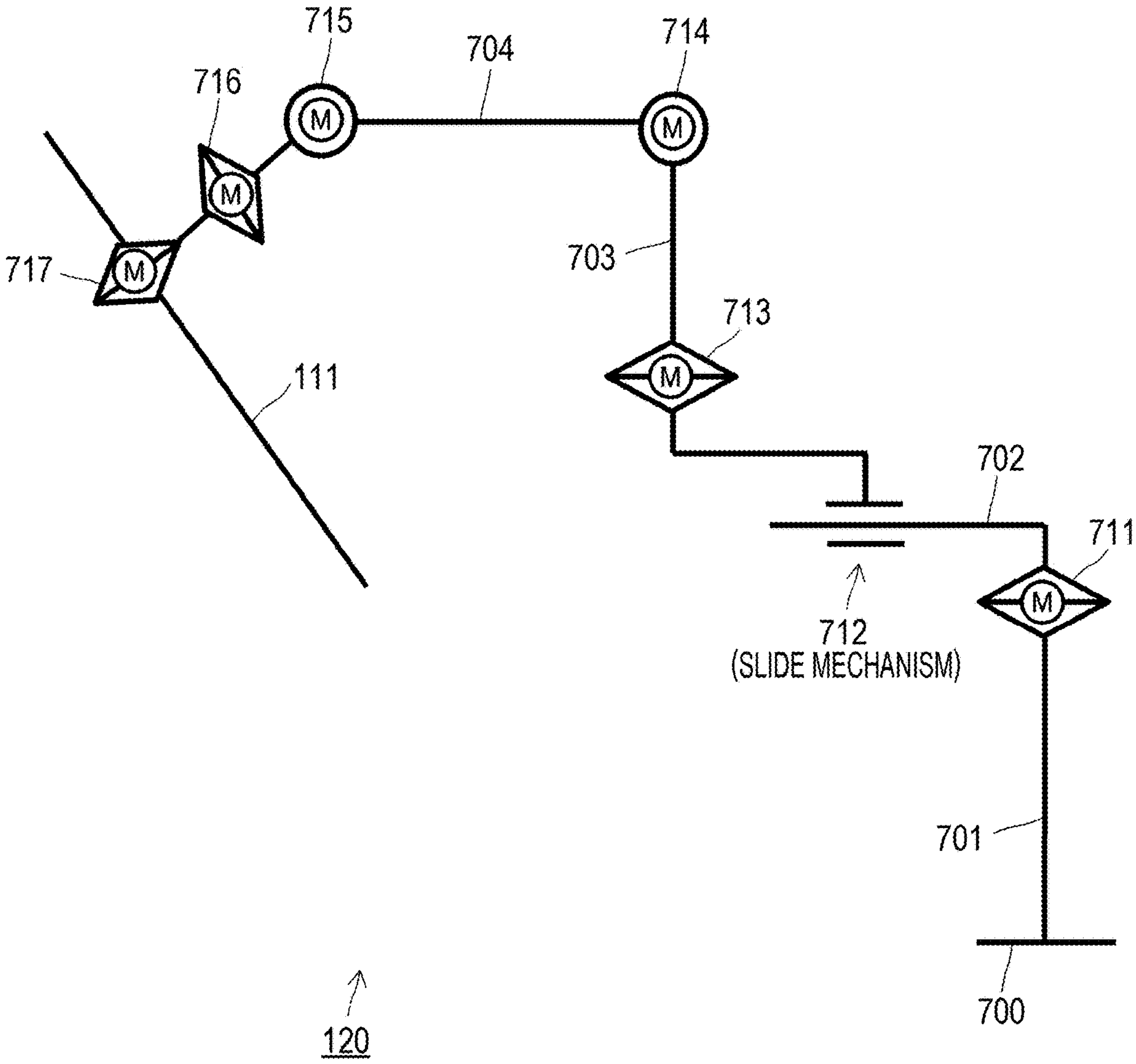
FIG. 14 is a diagram illustrating an arrangement example of active axes in the medical arm device 120.

FIG. 14 illustrates a degree-of-freedom configuration example in a case where all the rotation axes of the medical arm device 120 are set as active axes. However, the slide mechanism 712 may be either an active slide mechanism or a passive slide mechanism. In the medical arm device 120 illustrated in FIG. 14, actuators such as motors are mounted on six axes other than the linear motion axis, so that the endoscope 110 can be actively controlled with six degrees of freedom. Moreover, the position and direction in which the endoscope 110 accesses the abdominal cavity of the patient 103 can be adjusted by manually operating the passive slide mechanism 712 which is a linear motion axis.

Figure 15:
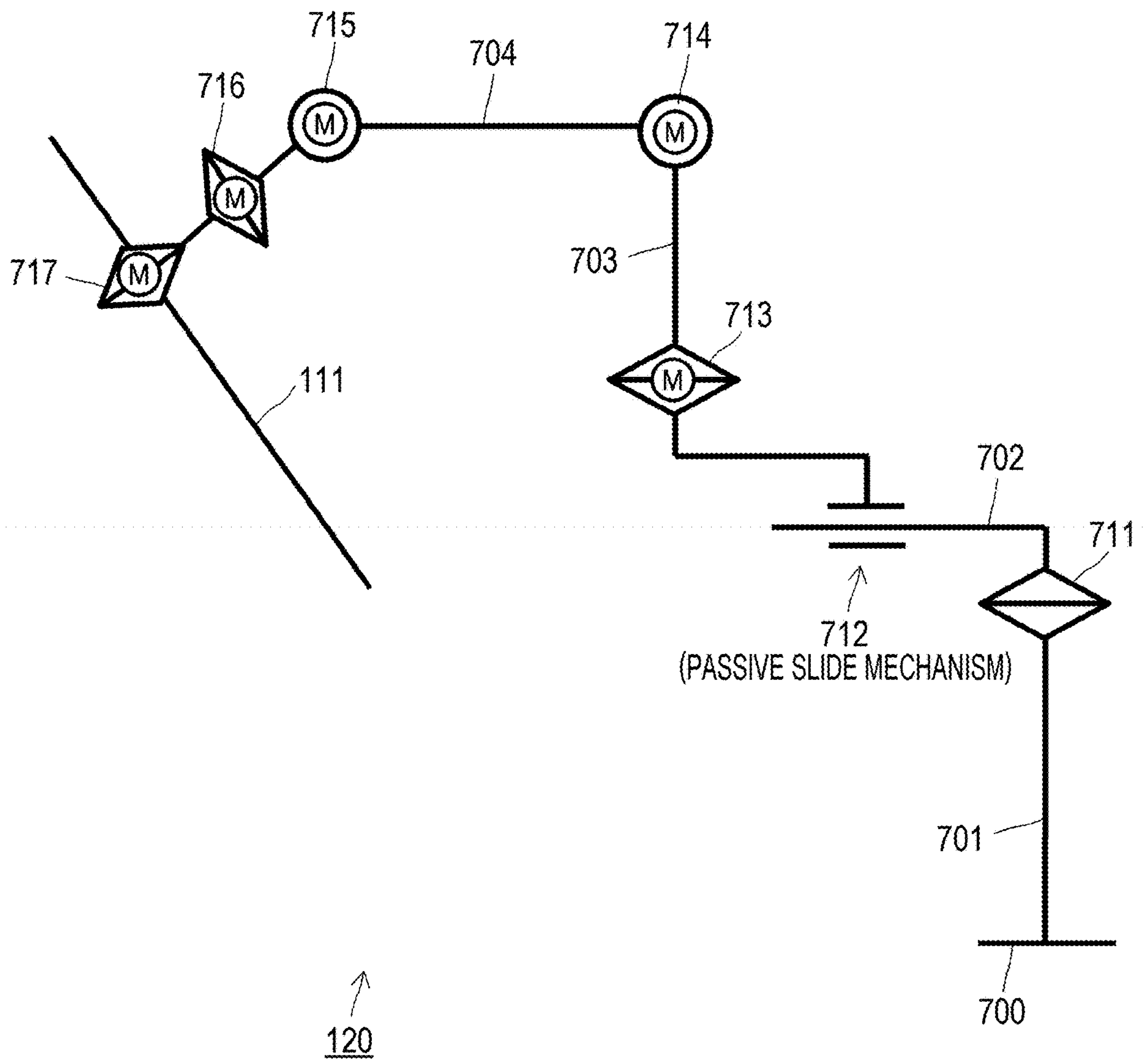
FIG. 15 is a diagram illustrating an arrangement example of active axes and passive axes in the medical arm device 120.

Furthermore, as a comparison with FIG. 14, FIG. 15 illustrates an arrangement example of active axes and passive axes in the medical arm device 120 in a case where some rotation axes are replaced with passive axes. In each drawing, a circled letter "M" is written on the active axis among the six rotation axes described above. In the example illustrated in FIG. 15, only the first joint part 711 which is the horizontal rotation axis of the root is a passive axis without the circled letter "M", and all the other rotation axes on the tip side are active axes.

In the arrangement example of the active rotation axes as illustrated in FIG. 15, the surgeon 101 and the assistant can manually adjust the rotational position (alternatively, the direction in which the second link 702 extends from the base part 700) of the first joint part 711 with respect to the base part 700 according to a direction in which the medical arm device 120 accesses the hand of the surgeon 101 and the like to avoid interference between the hand or arm of the surgeon 101 and the tip part of the arm.

Figure 16:
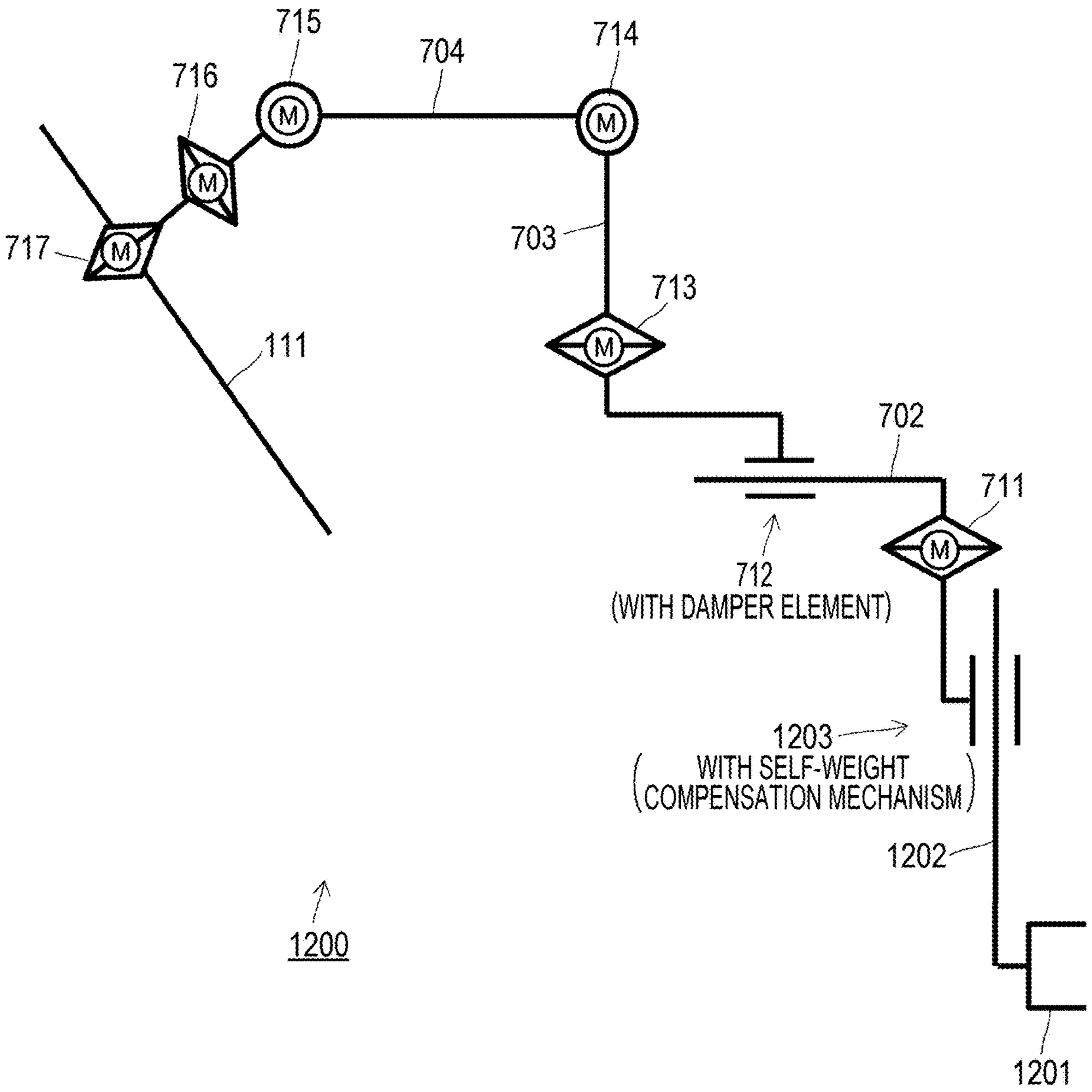
FIG. 16 is a diagram illustrating an arrangement example of active axes in the medical arm device 1200.

The arrangement examples of the active axes and the passive axes in FIGS. 14 and 15 are also applicable to the medical arm device 1200 illustrated in FIGS. 12 and 13. FIG. 16 illustrates a degree-of-freedom configuration example of the medical arm device 1200 having all rotation axes as active axes. Furthermore, FIG. 17 illustrates a degree-of-freedom configuration example of the medical arm device 1200 in which only the first joint part 711 is a passive axis and the other rotation axes on the tip side are active axes.

In the medical arm device 1200 illustrated in FIG. 16, actuators such as motors are mounted on six axes other than the linear motion axis, so that the endoscope 110 can be actively controlled with six degrees of freedom. Moreover, the position and direction in which the endoscope 110 accesses the abdominal cavity of the patient 103 can be adjusted by manually operating the passive slide mechanism 712 which is a linear motion axis.

Figure 17:
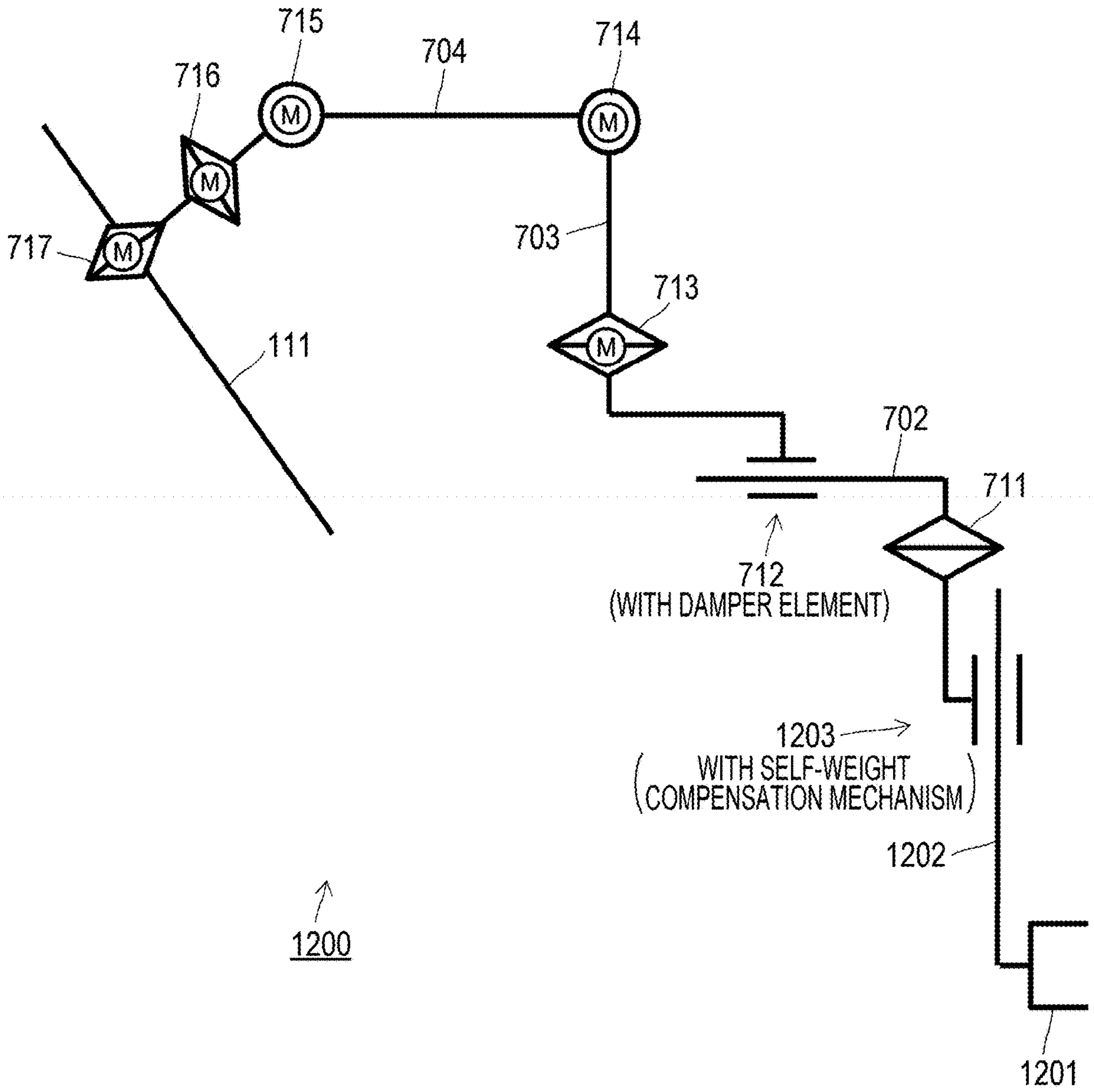
FIG. 17 is a diagram illustrating an arrangement example of active axes and passive axes in the medical arm device 1200.

On the other hand, in the medical arm device 1200 illustrated in FIG. 17, the surgeon 101 or the assistant can manually adjust the rotational position (alternatively, the direction in which the second link 702 extends from the base part 700) of the first joint part 711 with respect to the base part 700 according to a direction in which the medical arm device 120 accesses the hand of the surgeon 101 and the like, and can avoid interference between the hand or arm of the surgeon 101 and the tip part of the arm.

G-4. Medical Arm Device having Six Degree-of-Freedom Configuration

FIGS. 7, 8, and 11 illustrate the medical arm device 120 having a seven degree-of-freedom configuration, and FIGS. 12 and 13 illustrate the medical arm device 1200 having an eight degree-of-freedom configuration in which a linear motion axis for a lifting function is further added.

Figure 18:
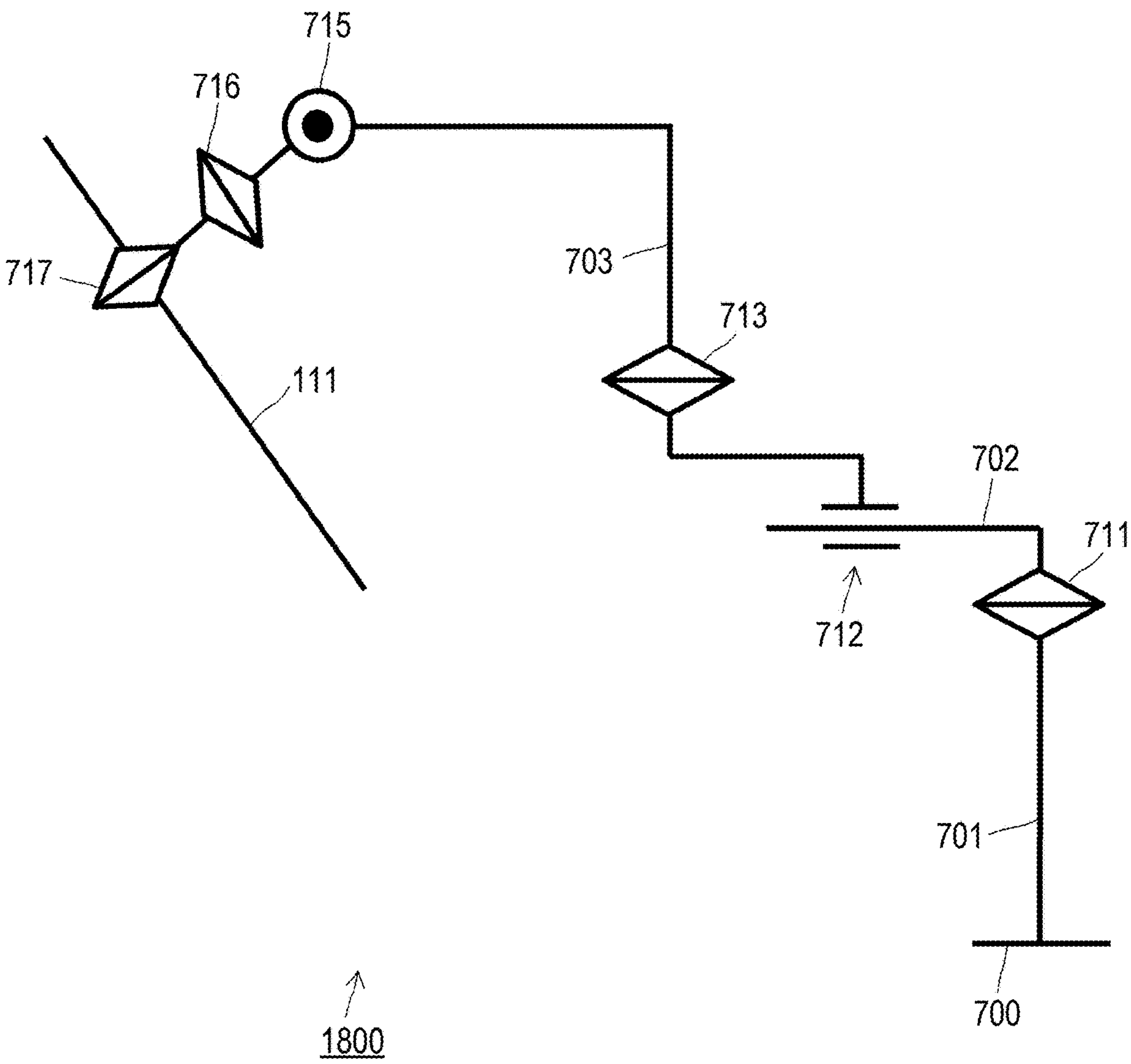
FIG. 18 is a diagram illustrating a degree-of-freedom configuration example of a medical arm device 1800.

FIG. 18 illustrates a degree-of-freedom configuration example of a medical arm device 1800 having 6 degrees of freedom as another example. Compared with the medical arm device 120 illustrated in FIG. 7, the medical arm device 1800 is different from the medical arm device 120 illustrated in FIG. 7 in that the third joint part 714 and the fourth link 704 are not included, and that the third link 703 has an L shape and supports the tip part including the endoscope 110 on a distal end side. The same components as those of the medical arm device 120 illustrated in FIG. 7 are denoted by the same reference numerals.

In a case where the laparoscopic surgery is performed using the medical arm device 1800, a length of each side of the L shape of the third link 703 is optimized, and a distance between the horizontal rotation axes of the root is adjusted using the slide mechanism 712, thereby coping with a change in the physique, posture, and affected part position of the patient 103.

Furthermore, since the medical arm device 1800 has only five rotation axes, insertion and removal of the endoscope 110 cannot be realized by an operation of the arm. For example, in a case where the physique of the patient 103 is large, it is assumed that a movable range of the medical arm device 1800 is insufficient and the insertion and removal operation of the endoscope 110 becomes difficult. Therefore, it is necessary to remove the endoscope 110 from the arm tip part and manually perform the insertion and removal operation. Furthermore, even if actuators such as motors are mounted on all the five axes other than the linear motion axis, the endoscope 110 can be actively controlled only with five degrees of freedom.

G-5. Regarding Arrangement of Linear Motion Axis

In the medical arm device 1200 illustrated in FIGS. 12 and 13, the first link 1202 on the root side includes a linear motion axis that can be operated in the vertical direction, and realizes the lifting-lowering mechanism 1203 that adjusts the height on the tip side. Therefore, the insertion and removal operation of the endoscope 110 becomes possible by operating the lifting-lowering mechanism 1203.

Figure 19:
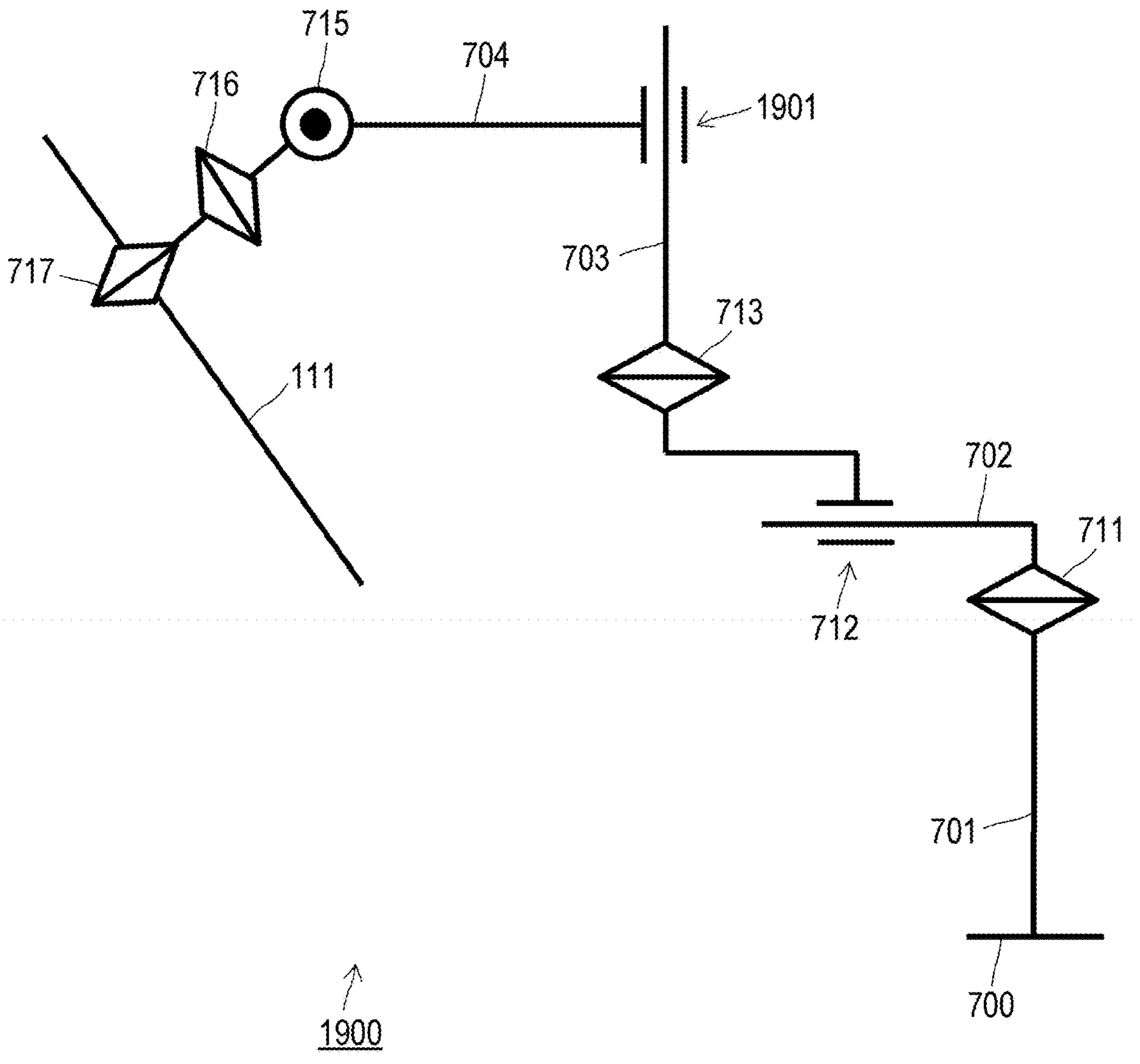
FIG. 19 is a diagram illustrating a degree-of-freedom configuration example of a medical arm device 1900.

FIG. 19 illustrates a degree-of-freedom configuration example of another medical arm device 1900 having a lifting-lowering mechanism. Compared with the medical arm device 120 illustrated in FIG. 7, the medical arm device 1900 is different from the medical arm device 120 in that the third joint part 714 and the fourth link 704 are connected via a lifting-lowering mechanism 1901 including a linear motion axis that is movable in the vertical direction instead of the rotation axis. The same components as those of the medical arm device 120 illustrated in FIG. 7 are denoted by the same reference numerals.

Also in the medical arm device 1900, the endoscope 110 can be inserted and removed by operating the lifting-lowering mechanism 1901. Furthermore, by adding the linear motion axis operable in the vertical direction to the intermediate part of the main body of the medical arm device 1900, the insertion and removal operation of the endoscope 110 can be realized without increasing a size of the tip part.

The lifting-lowering mechanism 1901 has a passive axis configuration without a driving actuator. The self-weight of the tip side acts on the passive axis. A self-weight compensation mechanism that compensates for the self-weight is incorporated in the passive axis so that the lifting-lowering mechanism 1901 does not lower due to the self-weight.

G-6. Configuration Example of Medical Arm Device having Redundant Degrees of Freedom As described above, in the medical arm device having the minimum six degrees of freedom, there may be a case where the insertion and removal operation of the endoscope is difficult due to the patient's physique and the like. However, in the medical arm device having seven degrees of freedom, the attitude of the endoscope can be freely changed including the insertion and removal operation of the endoscope. Moreover, by providing eight or more redundant degrees of freedom, the medical arm device can easily cope with individual differences in the patient's physique and changes in the surgical method. Note that, if the actuators are also mounted on all the redundant axes, the weight of the entire medical arm device increases and the cost also increases. Therefore, the redundant joints may be passive joints to suppress weight and cost.

Figure 20:
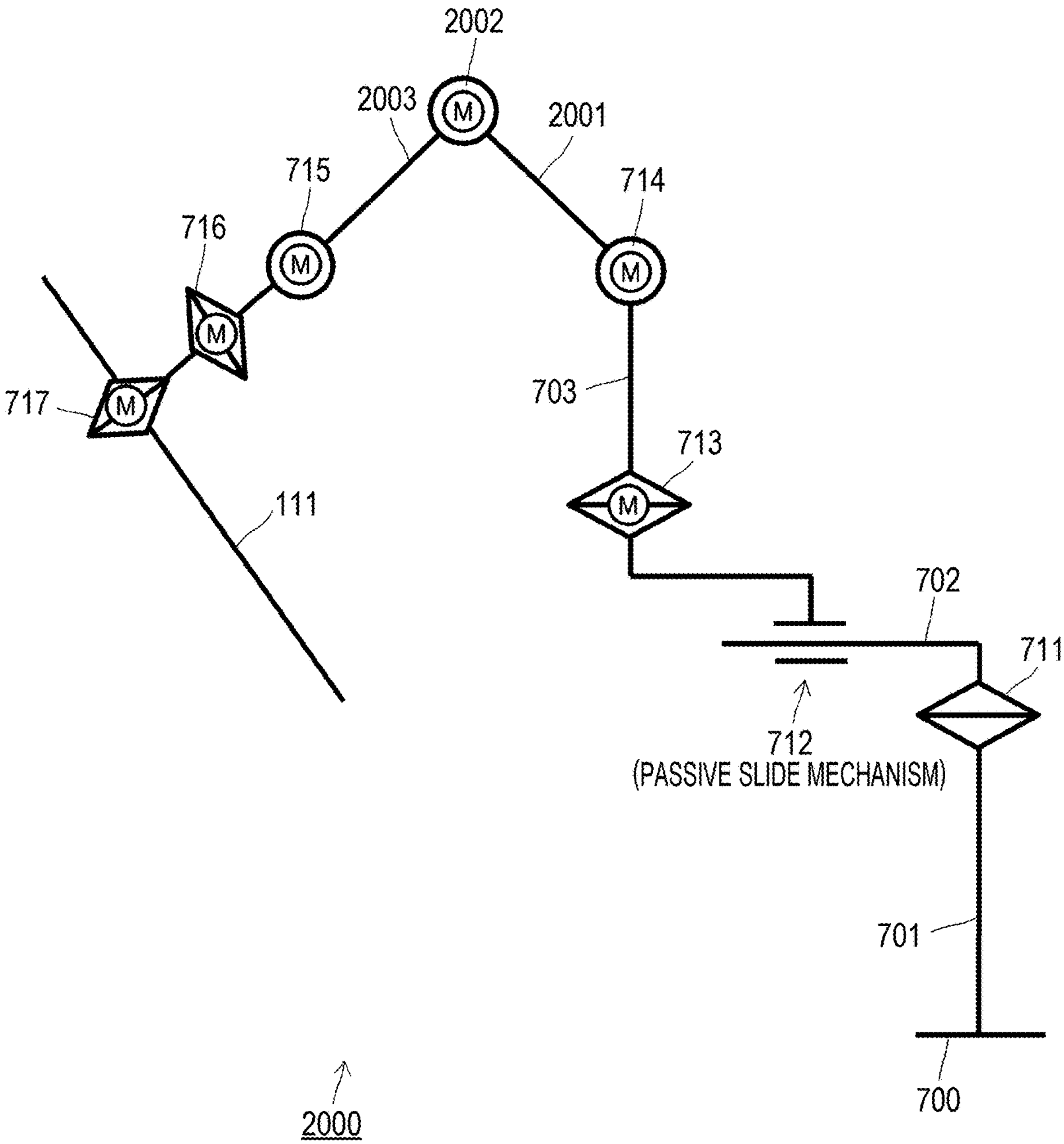
FIG. 20 is a diagram illustrating a degree-of-freedom configuration example of a medical arm device 2000.

FIG. 20 illustrates a degree-of-freedom configuration example of a medical arm device 2000 having a redundant degree of freedom. The medical arm device 2000 has three degrees of freedom of the tip part supporting the endoscope 110, three degrees of freedom of the second arm part including two horizontal rotation axes and a vertical axis for adjusting a distance between the horizontal rotation axes in the second arm part on a root side, and two degrees of freedom of two rotation axes of an intermediate part between the first arm part and the second arm part, and has a total of eight degrees of freedom.

The degree-of-freedom configurations of the first arm part and the second arm part are the same as those of the medical arm device 120 illustrated in FIG. 11, and the same components are denoted by the same reference numerals, and description thereof is omitted here. In the medical arm device 2000, a fourth link 2001 is attached to a tip of the third link 714 via the third joint part 714, a fifth link 2003 is attached to a tip of the fourth link 2001 via a fourth joint part 2002, and a tip part supporting the endoscope 110 is attached to a tip of the fifth link 2002.

The medical arm device 2000 is configured such that the first joint part 711 and the slide mechanism 712, which are two degrees of freedom on the root side, are passive axes, and all six degrees of freedom on the tip side after the second joint part 713 are active axes. By setting the two degrees of freedom on the root side as the passive axes, it is possible to reduce the weight of the entire medical arm device 2000.

At the time of initial setup of the surgery, two degrees of freedom of the passive axes on the root side are adjusted according to the physique of the patient 103, the surgical method, and the like. Of course, even during surgery, the two degrees of freedom of the passive axes on the root side may be readjusted as necessary. Thereafter, the position and attitude of the endoscope 110 can be actively controlled using 6 degrees of freedom of the active axes on the tip side.

Figure 21:
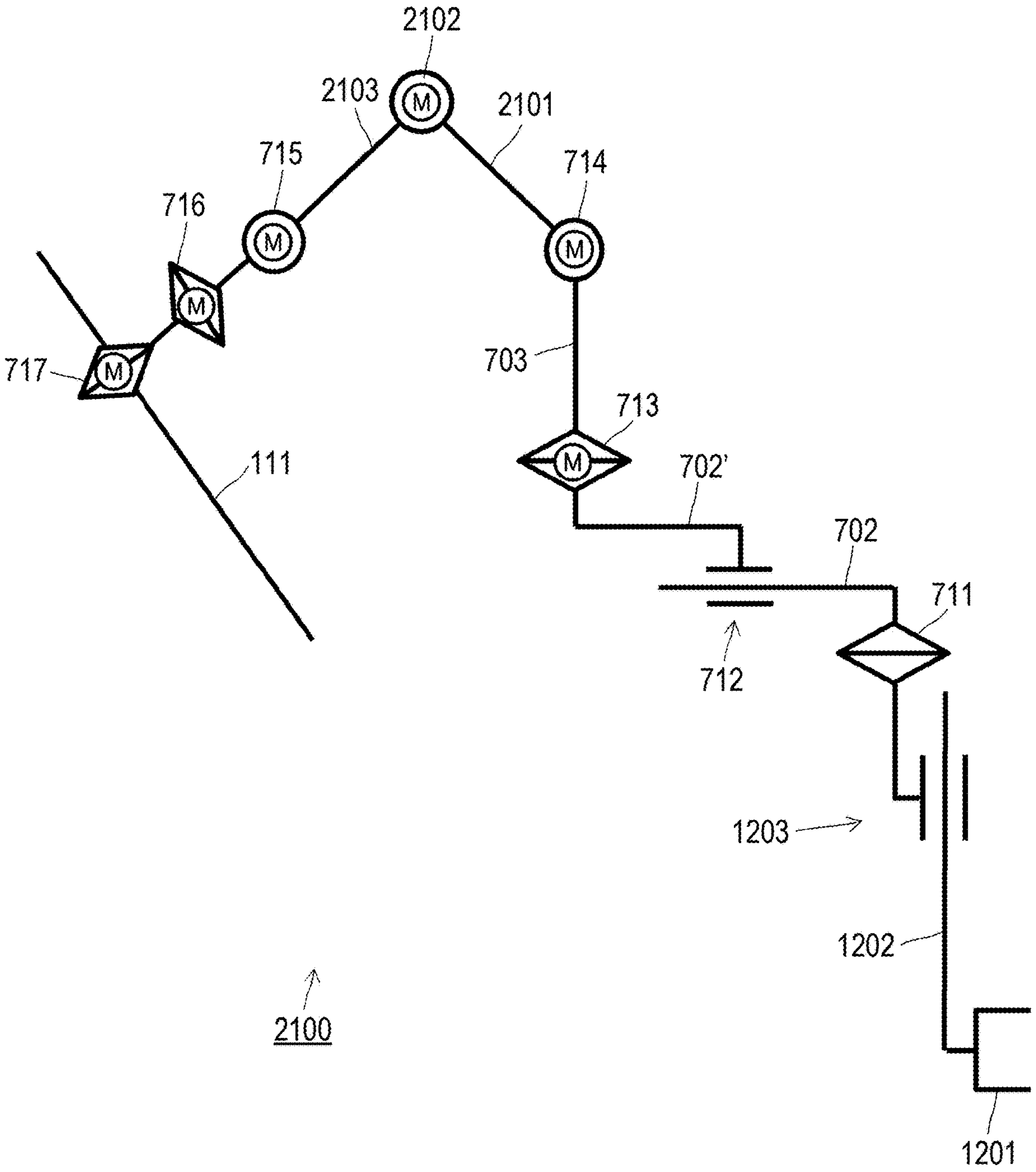
FIG. 21 is a diagram illustrating a degree-of-freedom configuration example of a medical arm device 2100.

FIG. 21 illustrates another degree-of-freedom configuration example of a medical arm device 2100 having a redundant degree of freedom. The medical arm device 2100 has three degrees of freedom of the tip part that supports the endoscope 110, four degrees of freedom of the second arm part including the two horizontal rotation axes, the vertical axis that adjusts the distance between the horizontal rotation axes, and the lifting-lowering mechanism, and two degrees of freedom of the two rotation axes of an intermediate part between the first arm part having the tip part and the second arm part, and has a total of 9 degrees of freedom.

The degree-of-freedom configurations of the first arm part and the second arm part are the same as those of the medical arm device 1200 illustrated in FIGS. 12 and 13, and the same components are denoted by the same reference numerals, and description thereof is omitted here. In the medical arm device 2100, a fourth link 2101 is attached to a tip of the third link 714 via the third joint part 714, a fifth link 2103 is attached to a tip of a fourth link 2101 via a fourth joint part 2002, and a tip part supporting the endoscope 110 is attached to a tip of the fifth link 2102.

The medical arm device 2100 is configured such that the first joint part 711, the slide mechanism 712, and the lifting-lowering mechanism 1203, which are three degrees of freedom on a root side, are passive axes, and all six degrees of freedom on the tip side after the second joint part 713 are active axes. By setting the three degrees of freedom on the root side as passive axes, it is possible to reduce the weight of the entire medical arm device 2100.

At the time of initial setup of the surgery, three degrees of freedom of the passive axes on the root side are adjusted according to the physique of the patient 103, the surgical method, and the like, or an attachment position to the surgical bed 102 is adjusted by moving the attachment structure part 1201 along the bed rail. Of course, also during surgery, the three degrees of freedom of the passive axes on the root side may be readjusted or the attachment position to the surgical bed 102 may be adjusted as necessary. Thereafter, the position and attitude of the endoscope 110 can be actively controlled using 6 degrees of freedom of the active axes on the tip side.

Figure 22:
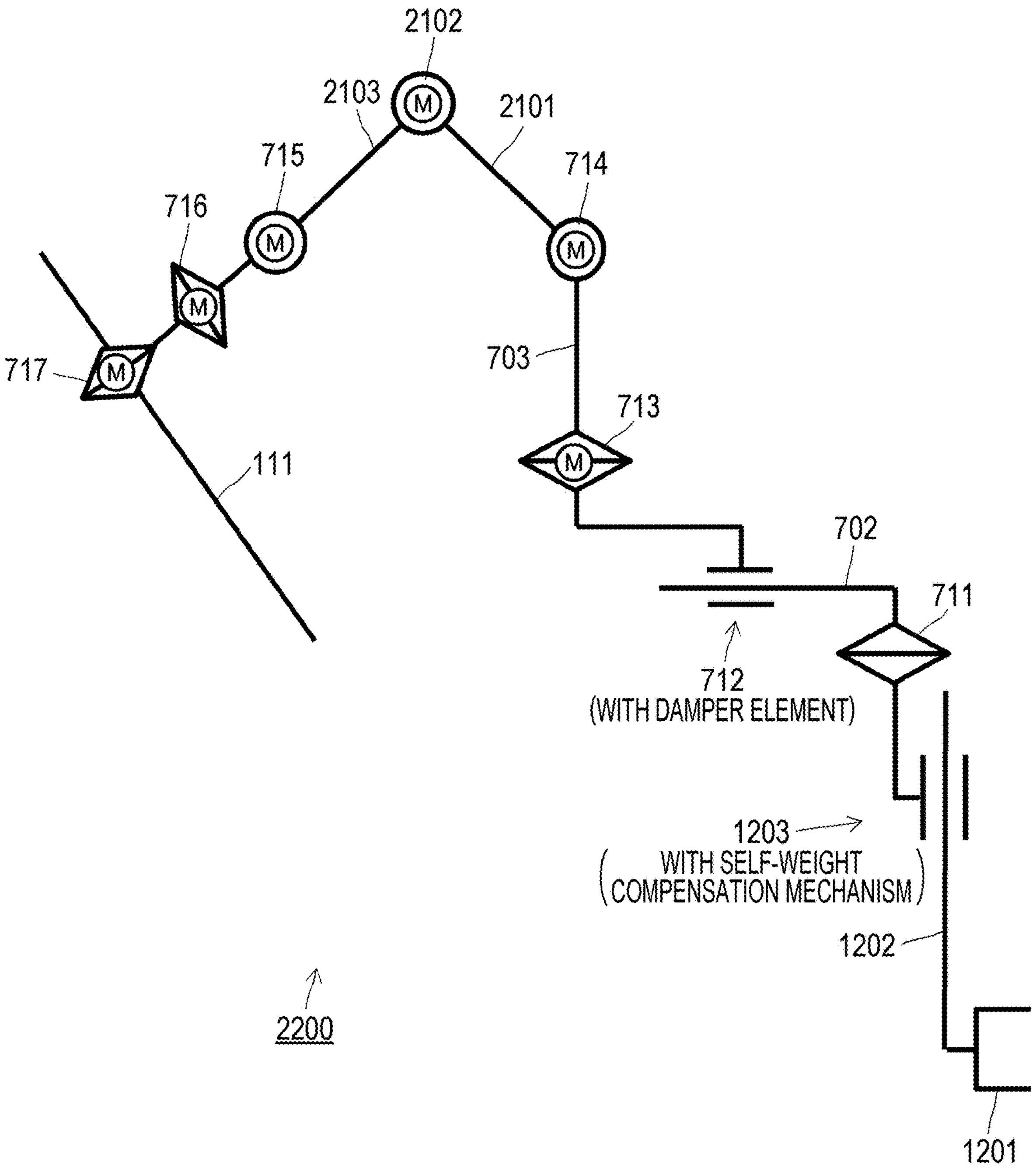
FIG. 22 is a diagram illustrating a degree-of-freedom configuration example of a medical arm device 2200.

FIG. 22 illustrates still another degree-of-freedom configuration example of a medical arm device 2200 having a redundant degree of freedom. The degree-of-freedom configuration of the medical arm device 2200 illustrated in FIG. 22 is the same as that of the medical arm device 2100 illustrated in FIG. 21, and the same components are denoted by the same reference numerals, and description thereof is omitted here. In the medical arm device 2200, a damper element is incorporated in the slide mechanism 712 which is a passive axis, and a self-weight compensation mechanism is incorporated in the lifting-lowering mechanism 1203. The configuration method of the damper element and the self-weight compensation mechanism is as described above.

Therefore, it is preferable to suppress a steep operation of the tip part, for example, when the surgical bed 102 is inclined by incorporating the damper element in the passive slide mechanism 712. Furthermore, by incorporating the self-weight compensation mechanism in the lifting-lowering mechanism 1203, it is possible to maintain the current height without lowering the tip side of the arm due to the self-weight. Therefore, the surgeon 101 and the assistant can perform the operation of the laparoscopic surgery without supporting the arm weight by hand.

Figure 23:
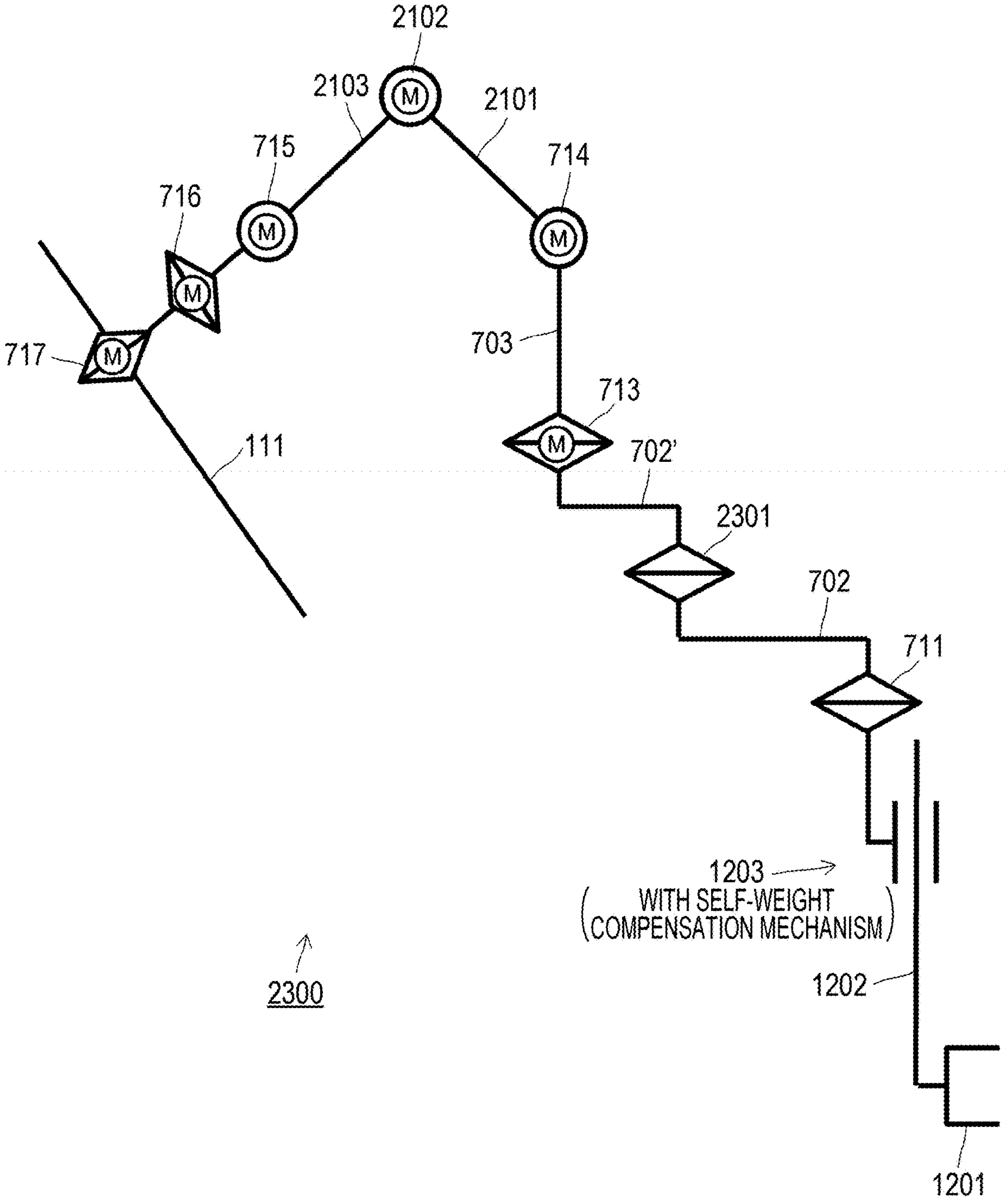
FIG. 23 is a diagram illustrating a degree-of-freedom configuration example of a medical arm device 2300.

FIG. 23 illustrates a modification example of a medical arm device 2300 having still another degree-of-freedom configuration. However, the same components as those of the medical arm device 2200 illustrated in FIG. 22 are denoted by the same reference numerals, and description thereof is omitted here. The medical arm device 2300 is different in that an inter-axis distance changing unit that changes a distance between the first joint part 711 and the second joint part 713, which are two horizontal rotation axes, is realized by a horizontal rotation axis 2301 instead of the slide mechanism 712. The horizontal rotation axis 2301 is inserted on a link connecting the first joint part 711 and the second joint part 713. A link connecting the first joint part 711 and the horizontal rotation axis 2301 is defined as a second link 702, and a link connecting the horizontal rotation axis 2301 and the second joint part 713 is defined as an additional link 702'.

Figure 24:
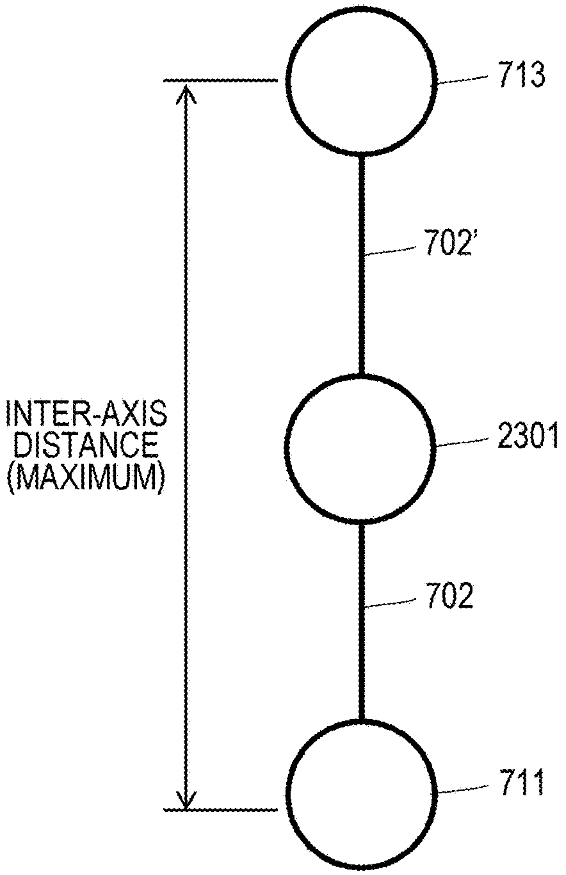
FIG. 24 is a diagram illustrating an operation example of an inter-axis distance changing unit including a horizontal rotation axis 2301.
Figure 25:
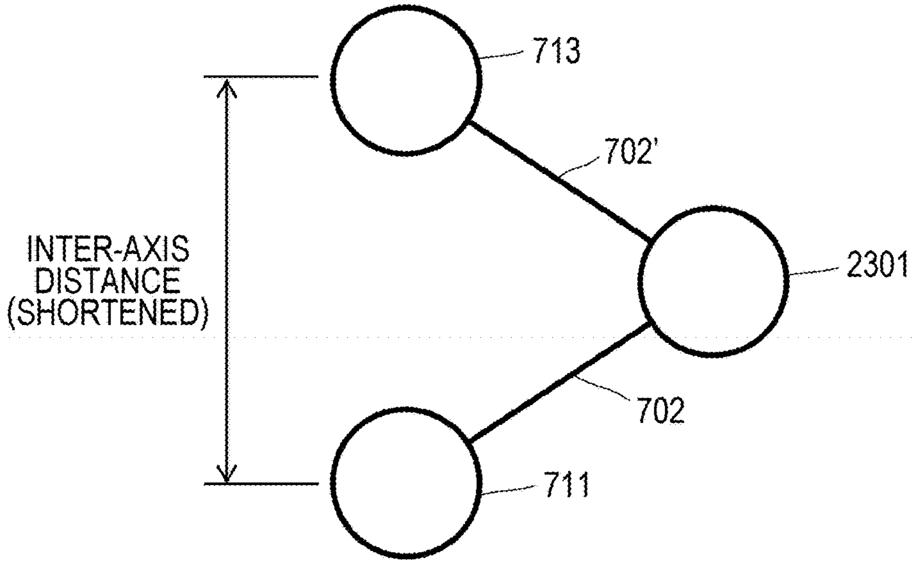
FIG. 25 is a diagram illustrating an operation example of the inter-axis distance changing unit including the horizontal rotation axis 2301.

FIGS. 24 and 25 illustrate a state where the first joint part 711, the second link 702, the horizontal rotation axis 2301, the additional link 702', and the second link 713 are looked down from above, and an inter-axis distance is changed by the rotation of the horizontal rotation axis 2301. As illustrated in FIG. 24, in the rotational position of the horizontal rotation axis 2301 where the second link 702 and the additional link 702' are straight, the inter-axis distance between the first joint part 711 and the second joint part 713 is maximized. Furthermore, when the horizontal rotation axis 2301 is rotated such that the two links 702 and the additional link 702' are bent, the inter-axis distance between the first joint part 711 and the second joint part 713 is shortened.

The horizontal rotation axis 2301 may be constituted by either an active axis that rotates by an actuator or a passive axis that rotates by an operation by a user (surgeon 101 or the like). In the latter case, the horizontal rotation axis 2301 preferably includes a damper element and is configured to be able to maintain the rotational position of the horizontal rotation axis 2301, that is, the inter-axis distance, when the user's hand is released.

H. Effects

The effects of the present disclosure will be summarized.

(1) A medical arm device according to the present disclosure has a multi-link structure having at least six degrees of freedom, in which the second arm part on the root side includes at least two horizontal rotation axes and the inter-axis distance changing unit that changes a distance between the two horizontal rotation axes, and the tip part has a structure in which orthogonal rotation axes of three degrees of freedom that determine an attitude of an endoscope are disposed (See FIGS. 7, 8, and 11 to 13.). Therefore, the medical arm device can control the endoscope with six or more degrees of freedom. The tip part supporting the endoscope can access hands of a surgeon from an opposite side of the surgeon (a region on a projection of the endoscope), and can avoid interference with the left and right hands and arms of the surgeon. Furthermore, the medical arm device can also avoid interference with an assistant and other equipment. Even if a link length is shortened, a reach range of the endoscope supported by the tip part can be expanded by adjusting the inter-axis distance changing unit of the second arm part. Furthermore, by shortening the link length, an output of the actuator that drives a joint can be reduced, and the weight of the entire medical arm device can be reduced.

(2) The medical arm device according to the present disclosure has a structure in which orthogonal rotation axes with three degrees of freedom in which the tip part determines an attitude of the endoscope are intensively disposed (See FIGS. 7 and 8.). Therefore, the medical arm device can realize downsizing of the tip part. Furthermore, it is possible to minimize the entry of the surgeon into the work space at hand and to avoid interference with the surgeon.

(3) In the medical arm device according to the present disclosure, an axis arrangement of the tip part has a structure in which the optical axis rotation axis of the endoscope, the left-right rotation axis, and the vertical rotation axis are disposed in order from the most tip part (See FIGS. 7 and 8.). Therefore, the movement of the arm at the time of an attitude change to the left and right can be minimized, and the influence on the interference with the surgeon can be suppressed.

(4) In the medical arm device according to the present disclosure, at least one of the three degrees of freedom on the root side is configured by a passive axis (See FIGS. 13, and 15 to 17.). By setting at least one degree of freedom on the root side as a passive axis, the weight of the entire medical arm device can be reduced.

(5) A medical arm device according to the present disclosure includes the lifting-lowering mechanism capable of adjusting a height of the second arm part (See FIGS. 12 and 13.). Therefore, the medical arm device can easily cope with a change in a quiet physique.

(6) A medical arm device according to the present disclosure has a structure attachable to a surgical bed (See FIGS. 12 and 13.). Therefore, when one degree of freedom of an attachment position to a bed rail is added and the inclination of the surgical bed is adjusted, a relative positional relationship between the patient and the medical arm device can be maintained.

(7) In the medical arm device according to the present disclosure, the damper element is incorporated in the passive axis (See FIG. 13.). Therefore, when the surgical bed is tilted, a steep operation of the tip part can be suppressed.

(8) In the medical arm device according to the present disclosure, the self-weight compensation mechanism is incorporated in the lifting-lowering mechanism that adjusts a height of the arm (See FIG. 13.). Therefore, it is possible to maintain the current height without lowering the tip side of the arm by the self-weight. Furthermore, the surgeon or the assistant can perform the operation of the laparoscopic surgery without supporting the arm weight by hand.

INDUSTRIAL APPLICABILITY

The present disclosure has been described in detail above with reference to specific embodiments. However, it is obvious that those skilled in the art can make modifications and substitutions of the embodiments without departing from the gist of the present disclosure.

In the present specification, the embodiments in which the present disclosure is applied to a medical arm device that supports an endoscope have been mainly described, but the gist of the present disclosure is not limited thereto. The present disclosure can be similarly applied to a medical arm device that supports a medical instrument other than the endoscope, for example, forceps, a pneumoperitoneum tube, an energy treatment tool, tweezers, a retractor, or the like at a tip, and an attitude of the medical instrument to be supported can be determined with three orthogonal degrees of freedom.

In short, the present disclosure has been described in the form of exemplification, and the contents described in the present specification should not be interpreted in a limited manner. In order to determine the gist of the present disclosure, the claims should be taken into consideration.

Note that the present disclosure can have the following configurations.

(1) A medical arm device including:
- a first arm part including a tip part that supports a medical instrument; and
- a second arm part that supports the first arm part, and includes at least two horizontal rotation axes and an inter-axis distance changing unit that changes a distance between the two horizontal rotation axes.

(2) The medical arm device recited in (1) described above, the medical instrument is an endoscope.

(3) The medical arm device recited in (1) or (2) described above, in which
- the second arm part includes a base part, a first link substantially perpendicularly attached to the base part, a first joint part having a degree of freedom around a horizontal rotation axis at a tip of the first link, a second link horizontally attached to the tip of the first link via the first joint part, and a second joint part having a degree of freedom around a horizontal rotation axis at a tip of the second link,
- the second link includes the inter-axis distance changing unit, and
- the first arm part is supported via the second joint part.

(4) The medical arm device recited in (3) described above, in which
- the inter-axis distance changing unit includes a slide mechanism that expands and contracts in a longitudinal direction of the second link.

(5) The medical arm device recited in (4) described above, in which the slide mechanism includes a damper element.

(6) The medical arm device recited in (3) described above, in which the inter-axis distance changing unit is a third joint part that bends the second link and has a degree of freedom around a horizontal rotation axis.

(7) The medical arm device recited in any one of (1) to (6) described above, in which the tip part includes a structure includes a structure in which joint members corresponding to rotation axes of three degrees of freedom that determine an attitude of the medical instrument are directly connected.

(8) The medical arm device recited in (7) described above, in which the tip part includes a structure in which a rotation axis around a longitudinal axis of the medical instrument, a yaw axis in a case where the rotation axis around the longitudinal axis is a roll axis, and a pitch axis are disposed in order from a most tip part.

(9) The medical arm device recited in (8) described above, in which the tip part includes a structure in which a distance between a joint corresponding to the rotation axis around the longitudinal axis and a joint corresponding to the pitch axis has a distance that does not cause interference when the tip part rotates around the pitch axis.

(10) The medical arm device recited in any one of (7) to (9) described above, in which the medical instrument is a medical observation device including an imaging unit, and the tip part includes a structure in which an optical axis rotation axis of the medical observation device, a pan axis that changes an observation direction of the medical observation device, and a tilt axis are disposed in this order from a most tip part.

(11) The medical arm device recited in any one of (3) to (10) described above, in which the second arm part includes an attachment structure part attached to a surgical bed.

(12) The medical arm device recited in any one of (3) to (10) described above, in which the first link includes a lifting-lowering mechanism.

(13) The medical arm device recited in (12) described above, in which the lifting-lowering mechanism includes a self-weight compensation mechanism.

(14) The medical arm device recited in any one of (3) to (13) described above, in which at least one of the first joint part, the second joint part, or the inter-axis distance changing unit includes a passive axis.

(15) The medical arm device recited in any one of (1) to (14) described above, further including a lifting-lowering mechanism provided between the first arm part and the second arm part.

(16) The medical arm device recited in (15) described above, in which the lifting-lowering mechanism includes a self-weight compensation mechanism.

REFERENCE SIGNS LIST

100 Endoscopic surgery system
101 Surgeon
102 Surgical bed
103 Patient
110 Endoscope
111 Lens barrel
112 Camera head
120 Medical arm device
130 Medical instrument group
131, 132, . . . . Medical instrument
140 Cart
141 CCU
142 Light source device
143 Arm control device
144 Input device
145 Treatment tool control device
146 Air film device
147 Recorder
148 Printer
149 Display device
151, 152, . . . . Trocar
201 Lens unit
202 Imaging unit
203 Drive unit
204 Communication unit
205 Camera head control unit
211 Communication unit
212 Image processing unit
213 Control unit
220 Transmission cable
300 Oblique-viewing endoscope
301 Eyepiece unit
302 Light guide connector
610 Passive joint unit
611 Encoder
620 Active joint unit
621 Actuator
622 Torque sensor
623 Encoder
630 Passive slide mechanism
631 Sensor
700 Base part
701 First link
702 Second link
703 Third link
704 Fourth link
711 First joint part
712 Slide mechanism
713 Second joint part
714 Third joint part
715 Vertical rotation axis part
716 Horizontal rotation axis part
717 Optical axis rotation axis part
1200 Medical arm device
1201 Attachment structure part
1202 First link
1203 Lifting-lowering mechanism
1210 Bed rail
1800 Medical arm device
1900 Medical arm device
1901 Lifting-lowering mechanism
2000 Medical arm device
2001 Fourth link
2002 Fourth joint part
2003 Fifth link
2100 Medical arm device
2101 Fourth link
2102 Fourth joint part
2103 Fifth link

The invention claimed is:

1. A medical arm device comprising:

a first arm part including a tip part that supports a medical instrument;

a second arm part that supports the first arm part having at least two rotation axes enabling horizontal planar rotation and an inter-axis distance changing mechanism configured to change a distance between the two rotation axes, wherein the second arm part includes a first link, a first joint part having a degree of freedom around a first rotation axis of the at least two rotation axes at a tip of the first link, a second link horizontally attached to the tip of the first link via the first joint part, and a second joint part having a degree of freedom around a second rotation axis of the at least two rotation axes at a tip of the second link, the second link includes the inter-axis distance changing mechanism, wherein the second link is configured to expand and contract to change the distance between the first rotation axis and the second rotation axis, and the first arm part is supported via the second joint part; and an intermediate part that connects the first arm part and the second arm part, the intermediate part having a rotation axis orthogonal to the at least two rotation axes, wherein the tip part includes a structure in which the rotation axis around a longitudinal axis of the medical instrument, a yaw axis, and a pitch axis are disposed in order from a most distal part and are directly connected via joint members without an interposed link.

2. The medical arm device according to claim 1, wherein the medical instrument is an endoscope.

3. The medical arm device according to claim 1, wherein the inter-axis distance changing mechanism includes a slide mechanism that expands and contracts in a longitudinal direction of the second link.

4. The medical arm device according to claim 3, wherein the slide mechanism includes a damper element.

5. The medical arm device according to claim 4, wherein the inter-axis distance changing mechanism is a passive axis, and the damper element is configured to maintain a distance between the first rotation axis and the second rotation axis when a manual operation of the second link is released.

6. The medical arm device according to claim 1, wherein the inter-axis distance changing mechanism is a third joint part that bends the second link and has a degree of freedom around a third rotation axis of the at least two rotation axes.

7. The medical arm device according to claim 1, wherein the tip part includes a first joint has a combined volume smaller than a combined volume of a human wrist and hand.

8. The medical arm device according to claim 1, wherein a distance between the rotation axis around the longitudinal axis and the pitch axis is configured to avoid self-interference of the first arm part during rotation.

9. The medical arm device according to claim 1, wherein a distance between the first joint and the third joint has a distance that does not cause interference when the tip part rotates around the pitch axis.

10. The medical arm device according to claim 1, wherein the medical instrument is a medical observation device including an image sensor, the rotation axis around the longitudinal axis corresponds to an optical axis rotation axis of the medical observation device, the yaw axis corresponds to a pan axis that changes an observation direction of the medical observation device, and the pitch axis corresponds to a tilt.

11. The medical arm device according to claim 1, wherein the second arm part includes an attachment structure part attached to a surgical bed.

12. The medical arm device according to claim 1, wherein the first link includes a lifting-lowering mechanism.

13. The medical arm device according to claim 12, wherein the lifting-lowering mechanism includes a self-weight compensation mechanism.

14. The medical arm device according to claim 1, wherein at least one of the first joint part, the second joint part, or the inter-axis distance changing mechanism includes a passive axis.

15. The medical arm device according to claim 1, further comprising a lifting-lowering mechanism provided between the first arm part and the second arm part.

16. The medical arm device according to claim 15, wherein the lifting-lowering mechanism includes a self-weight compensation mechanism.

17. A medical arm device comprising:

a first arm part including a tip part that supports a medical instrument, wherein the tip part includes a first joint member having a first degree of freedom, a second joint having a second degree of freedom, and a third joint having a third degree of freedom, the first to third degrees of freedom being orthogonal to one another, and the first to third joints together determine an attitude of the medical instrument and are directly connected without interposing a link therebetween; and a second arm part that supports the first arm part, the second arm having at least two rotation axes enabling horizontal planar rotation and an inter-axis distance changing mechanism configured to change a distance between the at least two rotation axes, wherein the tip part includes a structure in which the rotation axis around a longitudinal axis of the medical instrument, a yaw axis, and a pitch axis are disposed in order from a most distal part and are directly connected via joint members without an interposed link.

18. The medical arm device according to claim 17, wherein a distance between the rotation axis around the longitudinal axis and the pitch axis is configured to avoid self-interference of the first arm part during rotation.

19. The medical arm device according to claim 17, wherein a distance between the first joint and the third joint has a distance that does not cause interference when the tip part rotates around the pitch axis.

20. The medical arm device according to claim 17, wherein the medical instrument is a medical observation device including an image sensor, the rotation axis around the longitudinal axis corresponds to an optical axis rotation axis of the medical observation device, the yaw axis corresponds to a pan axis that changes an observation direction of the medical observation device, and
the pitch axis corresponds to a tilt.

* * * * *